(12) United States Patent
Jean et al.

(10) Patent No.: US 9,964,498 B2
(45) Date of Patent: May 8, 2018

(54) ELECTROMAGNETIC STEAM ENERGY/QUALITY, FLOW, AND FLUID PROPERTY SENSOR AND METHOD

(71) Applicant: BAYLOR UNIVERSITY, Waco, TX (US)

(72) Inventors: Buford Randall Jean, Lorena, TX (US); Christopher Faulkner, Houston, TX (US); Brandon Herrera, Waco, TX (US)

(73) Assignee: BAYLOR UNIVERSITY, Waco, TX (US)

(*) Notice: Subject to any disclaimer, the term of this patent is extended or adjusted under 35 U.S.C. 154(b) by 106 days.

(21) Appl. No.: 14/851,814

(22) Filed: Sep. 11, 2015

(65) Prior Publication Data
US 2017/0074816 A1    Mar. 16, 2017

(51) Int. Cl.
*G01N 27/74*    (2006.01)
*G01R 33/12*    (2006.01)
*G01N 22/00*    (2006.01)
*G01K 1/00*    (2006.01)
*G01F 1/36*    (2006.01)

(52) U.S. Cl.
CPC .............. *G01N 22/00* (2013.01); *G01K 1/00* (2013.01); *G01F 1/36* (2013.01)

(58) Field of Classification Search
CPC ........... G01N 27/08; G01N 27/74; G01F 1/34
USPC ........................................ 324/204, 89, 200
See application file for complete search history.

(56) References Cited

U.S. PATENT DOCUMENTS

| 3,663,204 | A | * | 5/1972 | Jungwirth | C21C 7/10 266/210 |
| 4,635,832 | A | * | 1/1987 | Angerer | B22D 11/186 164/155.1 |
| 4,759,479 | A | * | 7/1988 | Tinnes | B22D 11/16 222/196 |
| 4,770,230 | A | * | 9/1988 | Tinnes | B22D 2/006 164/155.3 |
| 4,890,665 | A | * | 1/1990 | Vetterli | B22D 11/16 164/136 |
| 5,372,355 | A | * | 12/1994 | Henn | B22D 41/20 222/602 |
| 8,433,526 | B2 | | 4/2013 | Roy et al. | |
| 2015/0173565 | A1 | * | 6/2015 | Sandu | B01F 5/10 426/519 |
| 2015/0340105 | A1 | * | 11/2015 | Goldberg | G21B 1/17 376/100 |

(Continued)

OTHER PUBLICATIONS

Jean, "A Microwave Sensor for Steam Quality". 2008, IEEE Transactions on Instrumentation and Measurement, vol. 57, No. 4, Apr. 2008.

*Primary Examiner* — Giovanni Astacio-Oquendo
(74) *Attorney, Agent, or Firm* — Jackson Walker LLP

(57) ABSTRACT

The disclosure provides a sensor and method for the measurement of fluid properties, such as steam energy and steam quality, and/or multiphase and multicomponent fluids and their flow regime profiles in a single instrument, and in some embodiments can include the mass flow rate. The invention can incorporate an orifice function that permits the measurement of fluid energy and a flow profile across at least a portion of the flow path with an electromagnetic sensing method combined with a standard mass flow rate measurement using an orifice differential pressure measurement system.

15 Claims, 25 Drawing Sheets

(56) References Cited

U.S. PATENT DOCUMENTS

2017/0016180 A1* 1/2017 Engstrom ................ D21C 7/10

* cited by examiner

ELECTROMAGNETIC STEAM ENERGY/QUALITY, FLOW, AND FLUID PROPERTY SENSOR AND METHOD

CROSS REFERENCE TO RELATED APPLICATIONS

Not applicable.

STATEMENT REGARDING FEDERALLY SPONSORED RESEARCH OR DEVELOPMENT

Not applicable.

REFERENCE TO APPENDIX

Not applicable.

BACKGROUND OF THE INVENTION

Field of the Invention

The disclosure relates generally to a system and method for measurement of the discernible properties of a fluid that relate to the composition of a fluid and the energy content of a fluid, such as steam, including a fluid attribute such as steam quality. More specifically, the disclosure relates to a system and method for measurement of the quality and related energy and composition properties of a fluid, such as steam, using electromagnetic waves.

Description of the Related Art

Fluid properties depend upon molecular composition, fluid phase and fluid internal energy state. The energy state for a given fluid phase can generally be described in terms of temperature and pressure. For example, steam energy is mainly composed of thermal energy as in heat and kinetic energy as in movement of atoms and molecules. Besides temperature and pressure as exemplary parameters for steam energy, another parameter for steam energy, which quantifies its composition with respect to phase, is steam quality. Steam quality quantifies the amount of condensed water present in saturated steam. Specifically, steam quality is defined as the mass ratio of saturated steam vapor to the total vapor plus condensate in a steam vapor- and liquid-water mixture. Although quality is an important process variable, it is not one that is easily measured in real-time. A standard method for measuring steam quality involves expensive and complicated calorimeter devices, as well as considerable time and effort. As a result, timely measurements of quality are often not available. Another standard method used in industrial settings is to measure the temperature and pressure at given points in a process flow and correlate those measurements to a database to predict the steam quality without actually measuring the quality. In the first method, the ability and time may not be available, such as in many industrial processes. In the second method that may be used for industrial processes, the accuracy may be insufficient. For example, steam turbines are operated typically at less than optimum efficiency to allow a margin of error for inaccuracies in steam quality and avoid large-scale damage. An example of such operation is described in U.S. Pat. No. 8,433,526 B2, entitled "Method and System for Steam Quality Monitoring", where the Abstract states:

A method of determining a steam quality of a wet steam located in an interior of a steam turbine includes emitting from an optical probe a plurality of wavelengths through the wet steam, measuring with the optical probe a wet steam intensity corresponding to each of the plurality of wavelengths emitted through the wet steam, determining an intensity ratio vector by dividing the wet steam intensity by a corresponding dry steam intensity for each of the plurality of wavelengths, successively applying scaling factors to the intensity ratio vector to obtain a scaled intensity ratio vector, calculating a suitable value for each of the scaling factors to obtain a plurality of residuals, determining a minimum residual of the plurality of residuals, determining a droplet size distribution by calculating the droplet number density corresponding to the minimum residual, and determining the steam quality based on the droplet size distribution.

It is well known that electromagnetic ("EM") energy can be applied to materials and the resulting response comprising energy passing through or reflected from the material can be measured to indicate properties of the materials. Electromagnetic properties of materials are frequency dependent. Information about the composition of the substance can be obtained by exposing the substance to EM energy at different frequencies and analyzing the response as a function of frequency. The term "permittivity" describes how a material responds to an applied electric field. Permittivity is determined by the ability of a material to polarize in response to an externally applied field so as to reduce the total electric field inside the material. Permittivity is often expressed as a relative value which is the ratio of the complex permittivity to the permittivity $\varepsilon_0$ of a vacuum. The response of natural materials to external EM fields depends on the frequency of the field, because the material's polarization does not respond instantaneously to an applied field. Permittivity for materials is expressed as a complex function to allow specification of the energy storage property and energy dissipation property of the material as a function of the angular frequency ($\omega$) of the applied field by means of real and imaginary components, respectively, as follows:

$$\varepsilon_r(\omega) = \varepsilon_r'(\omega) - j\varepsilon_r''(\omega)$$

Magnetic permeability, as another form of a material's response to applied EM energy, can be compared with electrical permittivity in that it is the degree of magnetization of material from reordered magnetic dipoles in the material when responding to a magnetic field applied to the material. Magnetic permeability is often expressed as a relative permeability to permeability $\mu_0$ in a vacuum. Magnetic permeability is also frequency dependent and can include real and imaginary components.

The dielectric properties of water have been measured and vary considerably based on the thermodynamic state of the water. At 100° C., the real part of the static relative permittivity of water changes from approximately 56 for the liquid phase to approximately 1.012 as a gas. However, the typical range in the permittivity values seen for a mixture of water and steam is much less than the large difference in the permittivities of liquid and vapor. This reduction in sensitivity is due to the fact that the permittivity of a mixture of molecules depends upon the relative volume occupied by each constituent. As a result, the permittivity of steam varies only from about 1.012 for dry steam to about 1.08 for 50% (x=0.5) steam quality at 100° C. and 175 psia. As temperature increases, the permittivities of both dry steam and water decrease. Increasing pressure typically increases the permittivity value.

There exists a significant need for a low cost, accurate, and robust sensing method and corresponding commercially viable instrument to measure fluid properties, including the energy of steam and related steam quality and other fluid parameters such as composition, using EM energy in a number of important energy production and industrial processing applications.

BRIEF SUMMARY OF THE INVENTION

The disclosure provides a sensor and method for the measurement of fluid properties, such as steam energy and steam quality, and/or multiphase and multicomponent fluids and their flow regime profiles in a single instrument, and in some embodiments can include the mass flow rate. The mass flow rate aspect of the invention is based upon an orifice function that permits the measurement of fluid energy and a flow profile across at least a portion of the flow path with an electromagnetic sensing method combined with a standard mass flow rate measurement using an orifice differential pressure measurement system.

The disclosure provides a system for determining steam energy in a vessel comprising: a steam energy sensor comprising one or more electromagnetic ("EM") resonators disposed at differing distances from a reference position of the sensor, the sensor being configured to be inserted into the vessel; a transmitter of EM energy configured to apply the transmitter EM energy to the one or more resonators in the vessel; a controller configured to control the transmitter EM energy; a receiver configured to receive responsive EM energy from one or more responses from the one or more resonators in the vessel; and a processor configured to receive data on the responsive EM energy from the receiver, compare the data from the receiver with predetermined data on steam energy, and determine the steam energy of steam at the sensor.

The disclosure also provides a method for determining steam energy in a vessel with a steam energy sensor comprising one or more electromagnetic ("EM") resonators disposed at differing distances from a reference position of the sensor, the sensor being configured to be inserted into the vessel; a transmitter of EM energy; a controller for the EM energy; a receiver of EM energy; and a processor, the method comprising: controlling an application of EM energy from the transmitter; transmitting the EM energy to the one or more EM resonators in the vessel; receiving responsive EM energy from one or more responses of the one or more EM resonators in the vessel; processing data on the responsive EM energy; comparing the data of the responsive EM energy with predetermined data on steam energy; and determining the steam energy of the steam at the sensor.

The disclosure further provides a system for determining fluid energy of a fluid in a vessel comprising: a fluid energy sensor comprising one or more electromagnetic ("EM") resonators disposed at differing distances from a reference position of the sensor, the sensor being configured to be inserted into the vessel; a transmitter of EM energy configured to apply the transmitter EM energy to the one or more resonators in the vessel; a controller configured to control the transmitter EM energy; a receiver configured to receive responsive EM energy from one or more responses from the one or more resonators in the vessel; and a processor configured to receive data on the responsive EM energy from the receiver, compare the data from the receiver with predetermined data on fluid energy, and determine the fluid energy of the fluid at the sensor. The vessel can define a flow path and the processor can be further configured to determine a fluid energy flow profile across at least a portion of the flow path with the one or more responses of the one or more resonators. The fluid energy sensor can include an orifice function configured to cause a pressure drop through a flow path in the vessel, and the system can further include a first pressure sensor configured to be disposed in the flow path upstream from the fluid energy sensor, a second pressure sensor configured to be disposed in the flow path downstream from the fluid energy sensor, and a processor configured to receive data on the pressures from the first and second pressure sensor and process the data to determine a mass flow rate of fluid through the flow path at the sensor. The fluid can include a mixture of molecules having different polarization levels that changes permittivity of the fluid based on the concentration of the mixture.

The disclosure can also provide a method for determining fluid energy in a vessel with a fluid energy sensor comprising one or more electromagnetic ("EM") resonators disposed at differing distances from a reference position of the sensor, the sensor being configured to be inserted into the vessel; a transmitter of EM energy; a controller for the EM energy; a receiver of EM energy; and a processor, the method comprising: controlling an application of EM energy from the transmitter; transmitting the EM energy to the one or more EM resonators in the vessel; receiving responsive EM energy from one or more responses of the one or more EM resonators in the vessel; processing data on the responsive EM energy; comparing the data of the responsive EM energy with predetermined data on fluid energy; and determining the fluid energy of the fluid at the sensor.

DETAILED DESCRIPTION

Figure 1A:
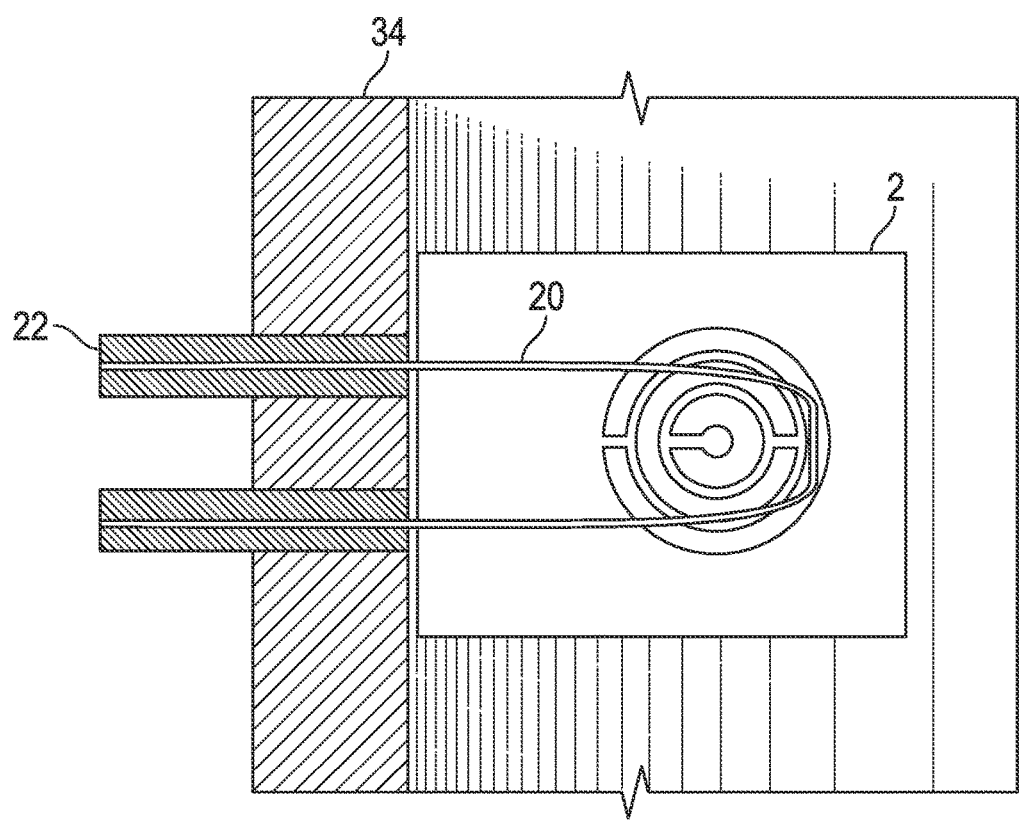
FIG. 1A is a schematic front view of an exemplary embodiment of a fluid energy sensor, such as a fluid quality sensor, according to the present invention configured such that it can be inserted as a probe into an open vessel, such as a pipe or other tubing, or into in a closed vessel, such as a tank or kettle.

The Figures described above and the written description of specific structures and functions below are not presented to limit the scope of what Applicant has invented or the scope of the appended claims. Rather, the Figures and written description are provided to teach any person skilled in the art how to make and use the inventions for which patent protection is sought. Those skilled in the art will appreciate that not all features of a commercial embodiment of the inventions are described or shown for the sake of clarity and understanding. Persons of skill in this art will also appreciate that the development of an actual commercial embodiment incorporating aspects of the present inventions will require numerous implementation-specific decisions to achieve the developer's ultimate goal for the commercial embodiment. Such implementation-specific decisions may include, and likely are not limited to, compliance with system-related, business-related, government-related and other constraints, which may vary by specific implementation, location and from time to time. While a developer's efforts might be complex and time-consuming in an absolute sense, such efforts would be, nevertheless, a routine undertaking for those of ordinary skill in this art having benefit of this disclosure. It must be understood that the inventions disclosed and taught herein are susceptible to numerous and various modifications and alternative forms.

The use of a singular term, such as, but not limited to, "a," is not intended as limiting of the number of items. Also, the use of relational terms, such as, but not limited to, "top," "bottom," "left," "right," "upper," "lower," "down," "up," "side," and the like are used in the written description for clarity in specific reference to the Figures and are not intended to limit the scope of the invention or the appended claims.

The disclosure provides a sensor and method for the measurement of fluid properties, such as steam energy and steam quality, and/or multiphase and multicomponent fluids and their flow regime profiles in a single instrument, and in some embodiments can include the mass flow rate. The mass flow rate aspect of the invention is based upon an orifice function that permits the measurement of fluid energy and a flow profile across at least a portion of the flow path with an electromagnetic sensing method combined with a standard mass flow rate measurement using an orifice differential pressure measurement system.

The description herein uses steam as an exemplary fluid. It is understood that other fluids can be used that have molecules with different levels of polarizability that would change permittivity measurements based on the composition percentage of the molecules with the different polarization energy levels. Because steam quality measurement involves a binary mixing relationship between fluids, here condensate (liquid water) and steam, the extraction of the fundamental measurement from the signals can be based upon resonant frequencies that are governed by a geometry of a flow path, sensor, and an interaction with the fluid in the flow path. The resonant frequency will generally be inversely proportional to the square root of the effective electrical permittivity of the fluid in the flow path. The effective permittivity depends upon the relative volumetric concentration of each constituent, that is the volumetric concentration of liquid water and steam vapor, and the permittivities of these components. The permittivities of the liquid and the vapor are each influenced by temperature and pressure. To some extent, the wetting of the sensor surfaces in the flow path may also have some effect on the observed resonant frequencies. Thus, direct modeling and to some extent computer modeling, can be used to help develop accurate and stable calibration for the steam quality sensor.

The present disclosure can map the information contained in complex permittivity functions into a signal-space that includes a series of nulls (or valleys) in a frequency domain representation, wherein the frequency location of each null is indicative of the value of the real part of the permittivity at that frequency. The quality factor of the null, as reflected in its depth and width, is indicative of the value of the imaginary part or loss factor of the permittivity.

It will be clear to those trained in the art that a sensor capable of measuring the complex electrical permittivity of a material will also be responsive to its magnetic permeability. In all of the descriptions herein that reference electrical permittivity, such descriptions have like applicability to magnetic permeability. Thus, the disclosure encompasses magnetic permeability as well and the term EM property is used particularly in the claims to reference both electrical permittivity and magnetic permeability.

The invention can use any suitable EM energy waveform over a wide band of frequencies through a material that is dispersive in nature. In some embodiments, the EM energy can be any signal having an appropriate bandwidth and amplitude and could be a wide band pulse, an ultra-wide-band (UWB) pulse, or a series of stepped frequencies. Further, a signal carrier, such as a high frequency carrier, can move the signal to a different band. Still further, a number of modulation schemes are possible, such as pseudorandom sequence modulation. High permittivity along the signal's transmission path produces a longer delay in transit time than does low permittivity. The dispersion properties of the wide band, coupled with time delay measurement, can provide the needed information for material properties. Dispersion of the signal energy is caused by the differential velocity profile as a function of frequency along the transmission path as well as a differential attenuation profile versus frequency. While the description below discusses a UWB pulse as exemplary and nonlimiting embodiments, it is understood that other forms of EM energy can be used to generate the information used for the output described herein.

Figure 1B:
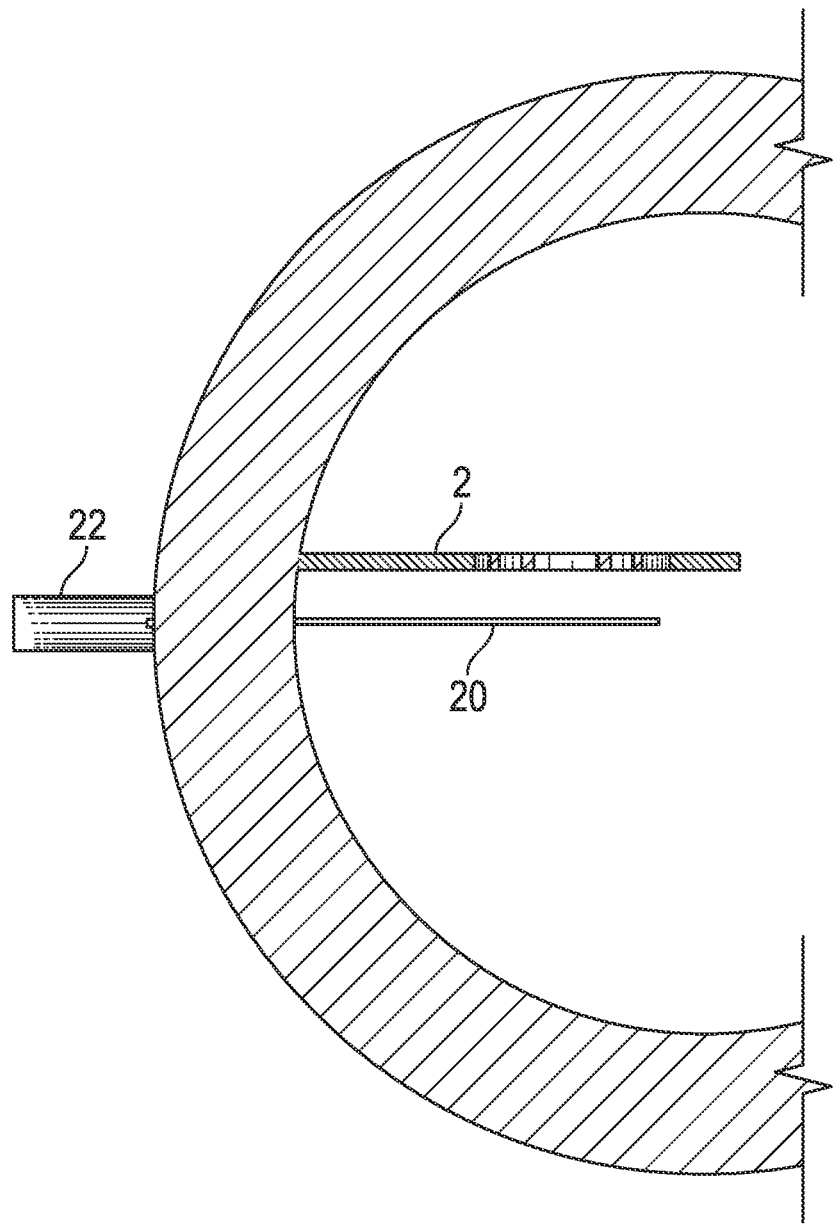
FIG. 1B is a schematic side view of the exemplary fluid energy sensor of FIG. 1A.
Figure 1C:
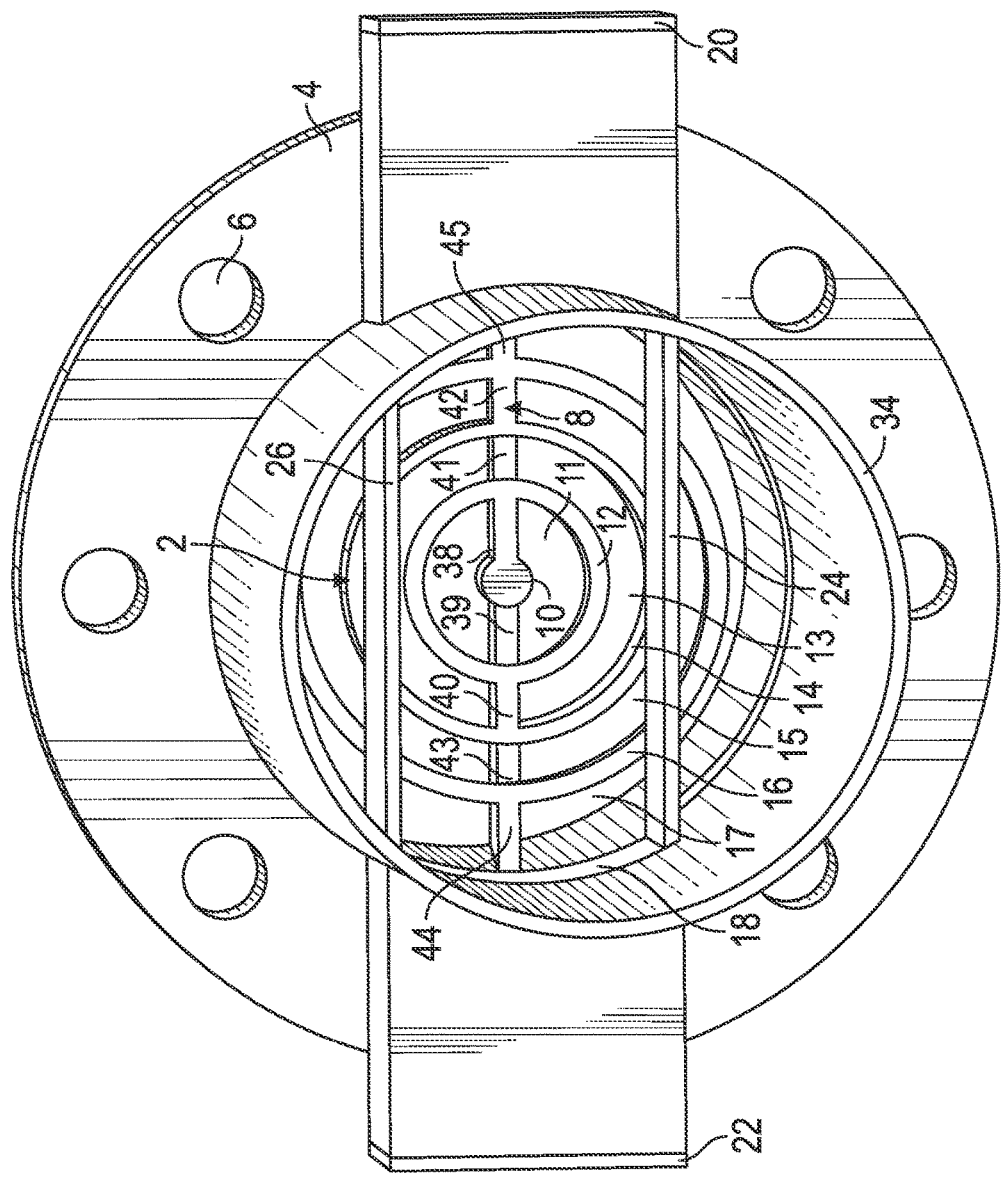
FIG. 1C is a schematic perspective view of an exemplary embodiment of a fluid energy sensor according to the present invention in an open vessel having a generally open flow path therethrough.
Figure 2:
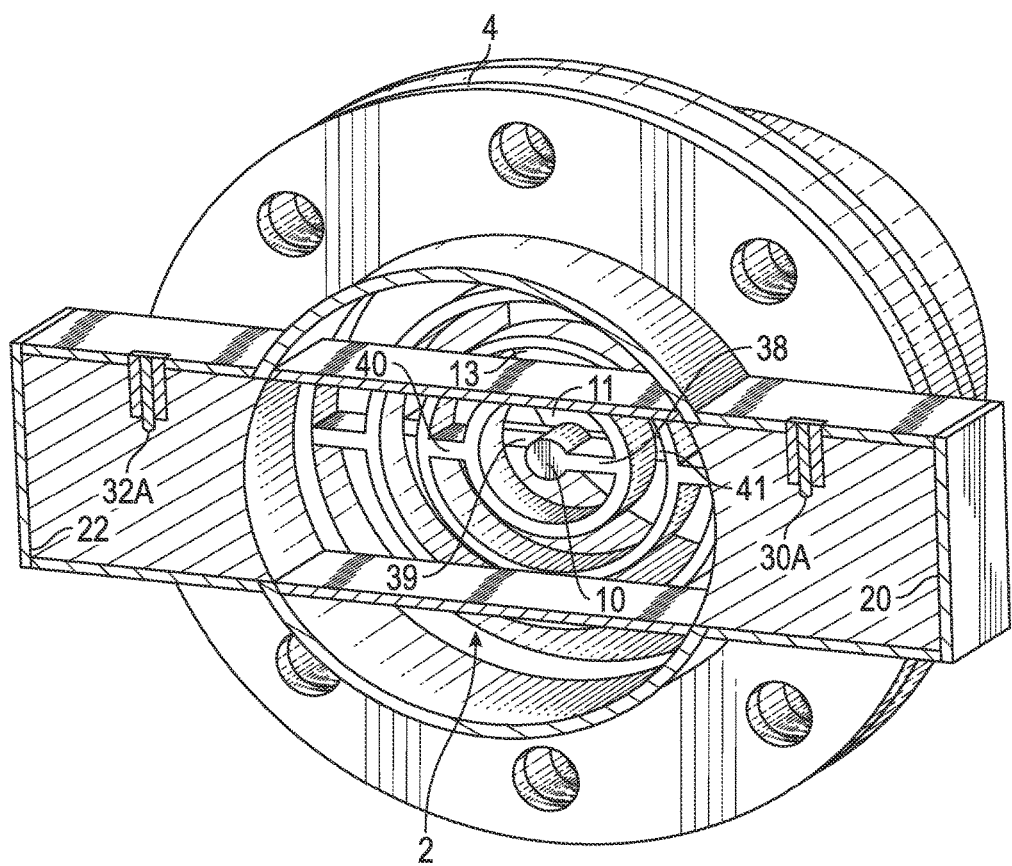
FIG. 2 is a schematic cross sectional perspective view through a transmitter and receiver portion of the sensor of FIG. 1.
Figure 3:
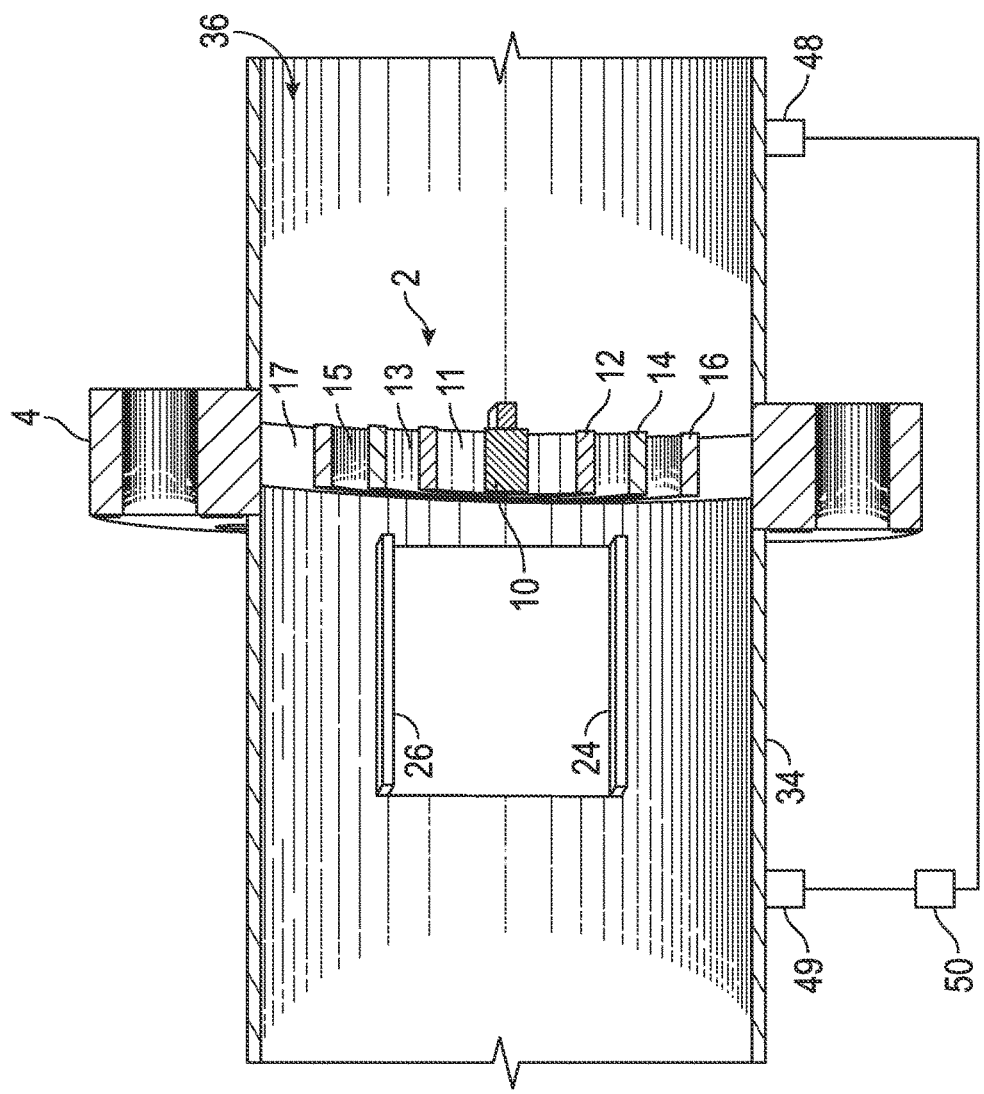
FIG. 3 is a schematic cross sectional side view of the sensor of FIG. 1.

FIG. 1A is a schematic front view of an exemplary embodiment of a fluid energy sensor, such as a fluid quality sensor, according to the present invention configured such that it can be inserted as a probe into a closed vessel, such as a pipe or other tubing, or into in a closed vessel, such as a tank or kettle. FIG. 1B is a schematic side view of the exemplary fluid energy sensor of FIG. 1A. FIG. 1C is a schematic perspective view of an exemplary embodiment of a fluid energy sensor according to the present invention in an open vessel having a generally open flow path therethrough. FIG. 2 is a schematic cross sectional perspective view through a transmitter and receiver portion of the sensor of FIG. 1B. FIG. 3 is a schematic cross sectional side view of the sensor of FIG. 1B. The figures will be described in conjunction with each other.

For the purposes of illustration, the fluid energy sensor will be described mainly as a steam energy sensor and more specifically in the form of a steam quality sensor, realizing that principles described herein can be adapted for other parameters of fluid energy, including other parameters for steam energy.

A steam quality sensor 2 can form a steam quality system of resonators with an orifice function in a fluid flow that allows the determination of steam quality, mass flow rate, and, in at least one embodiment, a flow regime across a profile of a dispersive medium, such as a flow path. The steam quality sensor 2 includes one or more resonators and a transmitter and receiver, described below, and in some embodiments can be used as an orifice for pressure drop and flow determination. The sensor 2 can be installed in a vessel 34. In some embodiments, a plate 4 can support the sensor 2 in the vessel 34. The vessel 34 can be "closed," where flow into or out of the vessel is generally closed during normal operation except for periodic opening to allow fluid in or out of the vessel, such as shown in FIGS. 1A and 1B. An exemplary closed vessel would be a tank, kettle, or container. The vessel 34 can also be "open," where the vessel is generally open during normal operation with a flow path 36, such as shown in FIG. 1C. An exemplary open vessel with a flow path could be a tube or pipe, with the understanding that valves could be used to periodically shut off the normal flow through the flow path.

One or more attachment holes 6 can be used for coupling the plate 4 with other structure (not shown), including other vessels. The attachment holes are only exemplary of an attachment means. Other types of connections include welded, threaded, slip on, being inserted into the vessel volume and secured to some structure, and other types of connections with the vessel. Also, various seals and gaskets can be used in the coupling of the plate, sensor, or a combination to the vessel.

One or more resonators can be disposed in the vessel and across the flow path, if present. While one resonator can be used to determine steam energy or quality, a plurality of resonators can advantageously establish a steam quality profile. A steam quality profile can be useful in a closed vessel at various positions in the vessel or in an open vessel across the flow path. In at least one embodiment, the resonators can be complementary split ring resonators. The complementary split ring resonators are formed by the annular space between structural members where the space is split by a support stiffener. The complementary split ring resonators between the structural members affects the resonance of the EM wave passing transmitted through the flow path. For example and without limitation, a sensor 2 can include a first ring divider 10, which can establish an exemplary reference position, and a second ring divider 12 that is disposed at a distance from the reference position. For example and without limitation, the second ring divider 12 can be radially disposed outward from the first ring divider 10 with an annular space therebetween. A support 8 with a stiffener 38 on one side of the first ring divider 10 couples the first ring divider 10 and the second ring divider 12. On another side of the first ring divider 10, the support 8 with a recessed stiffener 39 couples the first ring divider 10 and the second ring divider 12. The recessed stiffener 39 generally is disposed longitudinally in the flow path outside the space formed between the ring dividers. Thus, the annular space is divided by the stiffener 38, but not the recessed stiffener 39. The space between the first ring divider 10 and the second ring divider 12 that is split by the stiffener 38 is termed herein a first complementary split ring resonator 11.

Similarly, a third ring divider 14 is shown at a different distance from the exemplary reference position of the first ring divider 10 than the distance from the second ring divider 12. In the exemplary embodiment, the third ring divider 14 is radially disposed outward from the second ring divider 12 with a stiffener 40 and a recessed stiffener 41 coupling the second and third ring dividers to form a second complementary split ring resonator 13. Other ring dividers can be disposed at yet other distances from the reference position. For example, a fourth ring divider 16 is shown radially disposed outward from the third ring divider 14 with a stiffener 42 and a recessed stiffener 43 coupling the third and fourth ring dividers to form a third complementary split ring resonator 15. In the embodiment of the sensor 2 shown, the stiffeners and recessed stiffeners alternate in angular location, so that the split in the complementary split ring resonator is on alternating sides of the sensor across the vessel 34. A portion of the sensor disposed radially outward from the fourth ring divider 16 can function as a fifth ring divider 18 with a stiffener 44 and a recessed stiffener 45 coupling the fourth and fifth ring dividers to form a fourth complementary split ring resonator 17. The number of resonators can vary from one to several. For vessels 34 having a flow path, the resonators 11, 13, 15, 17 are disposed transversely across the flow path 36 as shown in this embodiment or longitudinally in other embodiments, such as the one shown in FIGS. 10 and 11. Other shaped sensors are contemplated with multiple split ring resonators generally disposed at differing distances from a reference portion of the sensor.

It has been observed that the liquid phase in steam migrates to the outside of a flow path for vertical flow and to the lower portions of a flow path for horizontal flow. Thus, it is advantageous to have a flow profile across the flow path. Further, the different dimensioned resonators can resonate at different frequencies. However, because steam has permittivity properties of vapor or water, each resonator will generally have a single resonance frequency for a given steam quality. The first complementary split ring resonator 11 can be disposed somewhat centrally to the flow path, with the second, third, and fourth complementary split ring resonators disposed progressively at farther radial distances from the resonator 11. Thus, the resonators can form a profile map of different values of steam energy, such as steam quality, across the flow path for better granularity of the steam quality. Similarly, a steam quality profile can be measured for a closed vessel at different positions in the vessel.

A transmitter housing 20, having a wave launching structure 30A, can be configured on one portion of the flow sensor 2. A receiver housing 22, having a wave receiving structure 32A, is disposed on a separate portion of the flow sensor generally distally across the flow path from the transmitter housing. In at least this embodiment, the wave launching structure 30A and the wave receiving structure 32A are coaxial and generate a coaxial waveguide excitation mode to propagate the electric component of an EM signal as a wave across the resonators. The housings 20, 22 can include ceramic material that can help propagate the transmission and reception of the signal from the wave launching structure 30 to the wave receiving structure 32. One or more wave guides, such as wave guides 24, 26, can guide the wave from the transmitter housing 20 with the receiver housing 22 and can be spaced a distance downstream or upstream from the resonators. The wave guides 24, 26 are used to help propagate the electromagnetic energy as a wave across the flow path between the transmitter housing 20 and the receiver housing 22. The wave launching structure 30A can produce a signal that is transmitted across the flow path along the wave guides 24, 26. The transmission of the signal has EM energy that is transmitted through the medium in the flow path to the resonators. As EM energy propagates as a wave, the wave couples across the resonators. The resonators respond and alter the transmitted signal that is received by the wave receiving structure 32A. At certain input signal frequencies, the resonators resonate in a harmonic frequency that drives the impedance of the resonators to a null value, effectively shorting the signal at that frequency. Other signal frequencies may not affect the resonators and where there is little to no effective impedance to the signal then the signal reaches a peak in frequency. Steam flowing in a dispersive medium, such as a flow path in a tube, changes EM permittivity based on the percentage of water in the steam. The varying permittivity changes the signal received by the wave receiving structure 32A. Thus, a "dry" steam, having little liquid water, can establish a first set of frequency nulls and peaks of the signal received by the receiver, while a wet steam having a higher amount of liquid water than the dry steam, can shift to a second set of frequency nulls and peaks that are different than the first set of frequency nulls and peaks for the dry steam. The frequency responses of the resonators for the nulls and peaks can be mapped to establish data of the sensor at different steam qualities. This predetermined data can be used to determine the steam quality in the vessel, such as by comparing results from the resonators while in use in the vessel with the predetermined data.

The exemplary steam quality sensor 2 also includes the function of an orifice to measure flow such as in the flow path 36. For an orifice to function, a reduction in the cross-sectional area of the flow path needs to occur, which causes a pressure drop and a change in velocity of the fluid in the flow path. The change in pressure is compared to the original pressure, and the difference can be used to calculate the volume of flow according to Bernoulli's principle, similar to a Venturi nozzle. Typically, an orifice plate is used for measuring a pressure drop for flow rates and is a relatively thin plate with a reduced diameter. However, the sensor 2 with the split rings and related structure in the flow path also function as a means for reducing the cross-sectional area of the flow path to cause a pressure drop and therefore function as an orifice in a flow path. To measure the pressure drop across the split rings and structure, the system can include a first pressure sensor 48 upstream from the sensor 2 and a second pressure sensor 49 downstream from the sensor 2. The output from the pressure sensors 48, 49 can be provided to a processor 50.

Thus, the sensor 2 can uniquely combine the function of an orifice with a steam quality sensor described above and measure both disparate properties with one instrument that requires one fitting or tap into a flow path.

Figure 4:
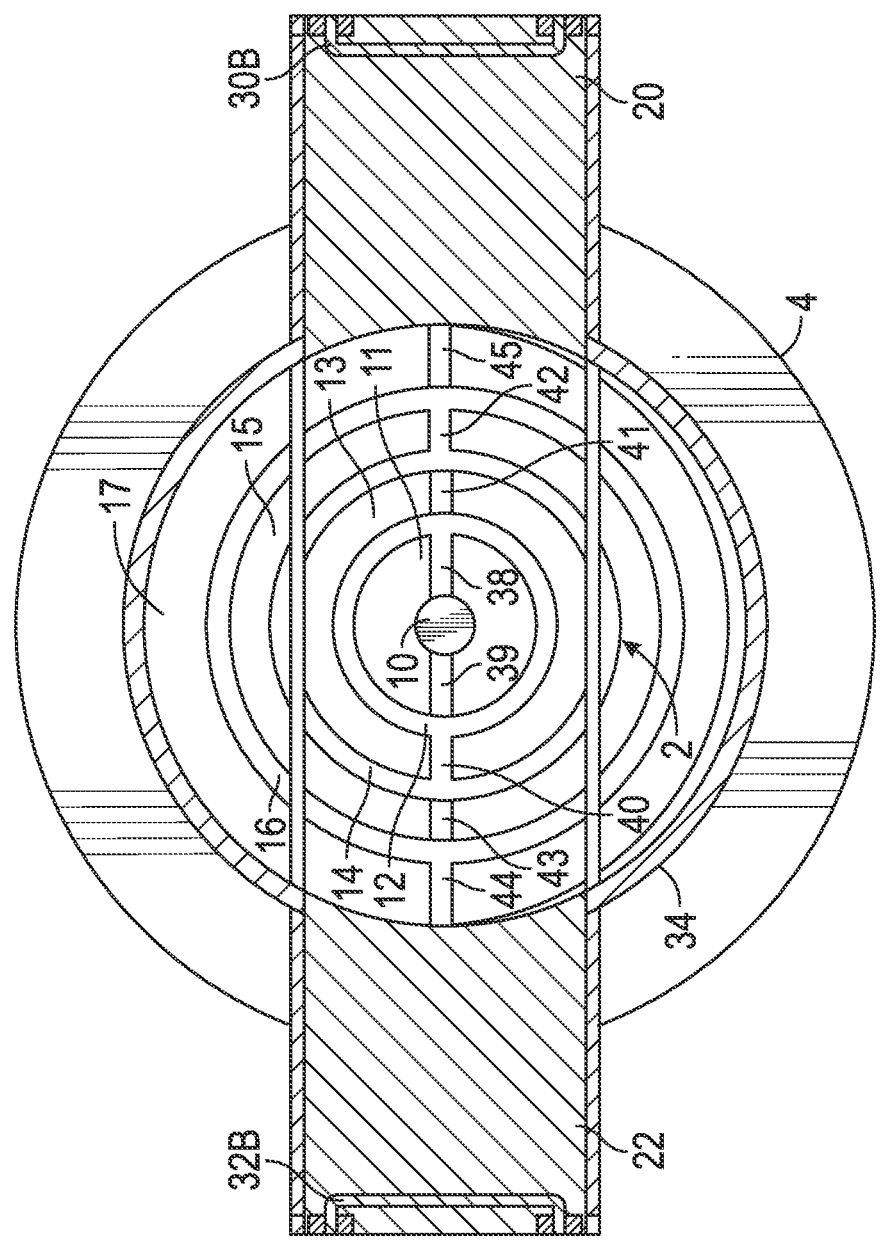
FIG. 4 is a schematic perspective view through an alternative embodiment of a transmitter and receiver portion of the sensor of FIG. 1.

FIG. 4 is a schematic cross sectional perspective view through an alternative embodiment of a transmitter and receiver portion of the sensor of FIG. 1. The alternative embodiment of the wave launching structure 30B and wave receiving structure 32B differs from the coaxial wave guide excitation embodiment, shown in FIG. 2. The wave launching structure 30B and wave receiving structure 32B, shown in FIG. 4, use a coupling loop excitation mode to propagate the magnetic component of an EM signal as a wave across the resonators. Other types of sensors and receivers can be used, as may be appropriate for the particular application.

Figure 5:
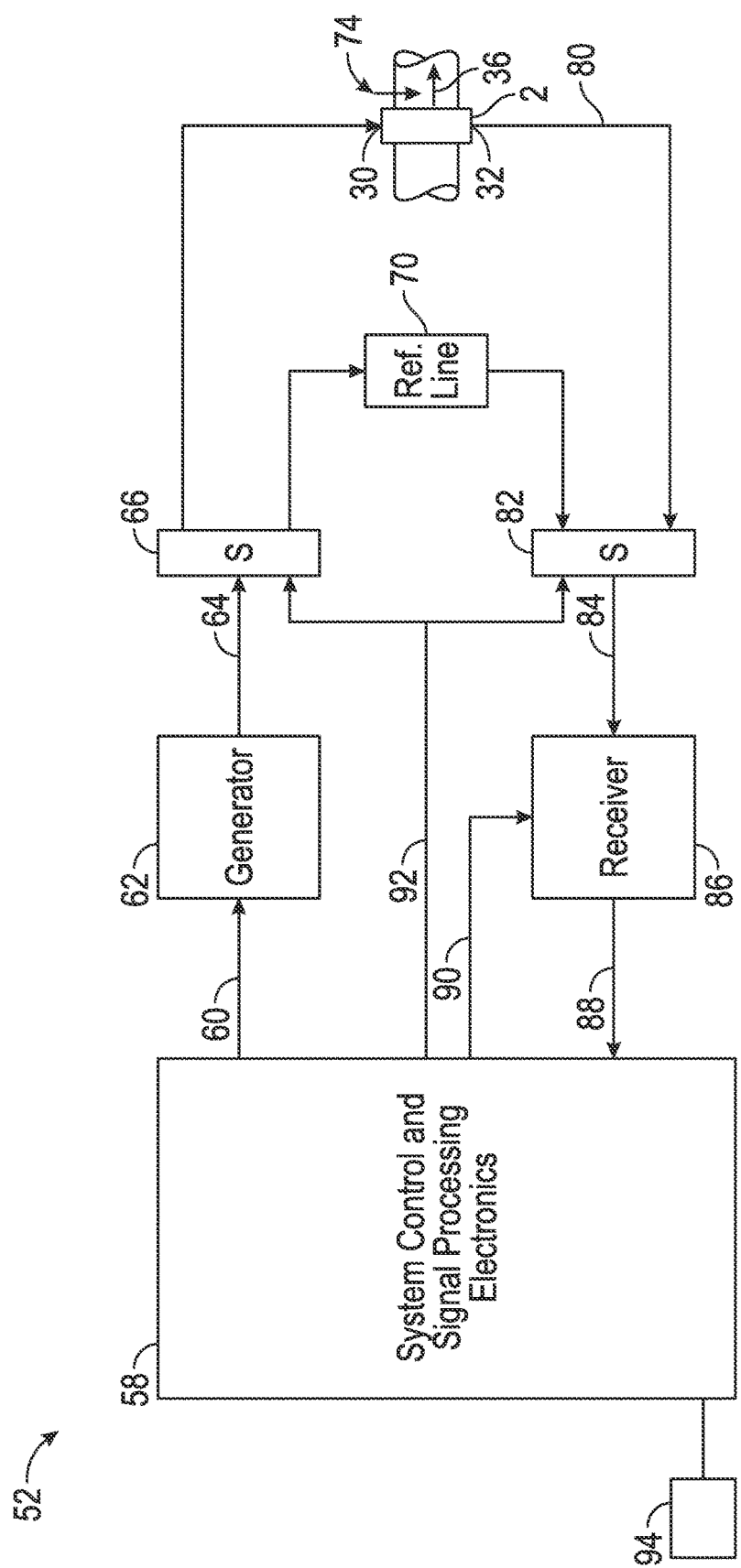
FIG. 5 is a block diagram of an exemplary embodiment of a sensor system.
Figure 6:
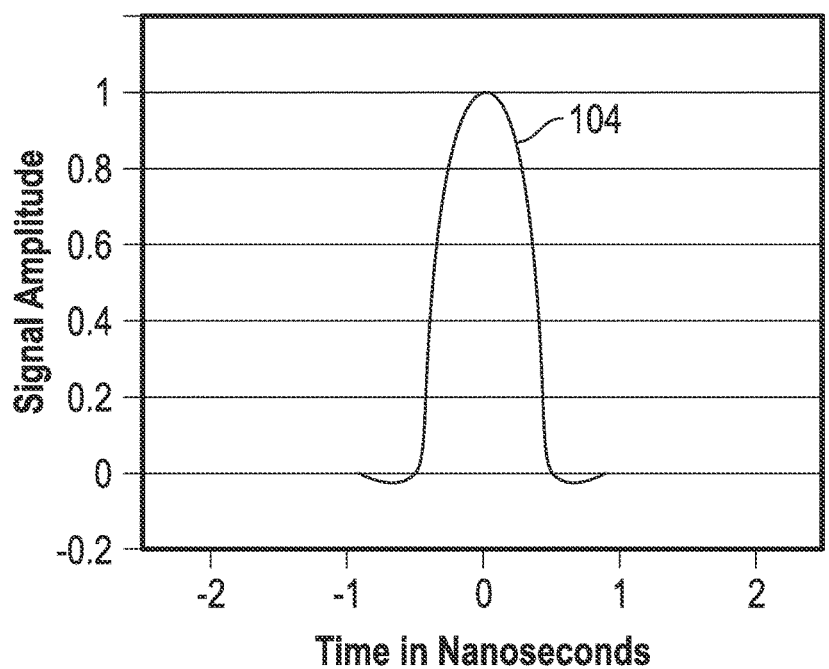
FIG. 6 is a graphical representation of an exemplary ultra-wide band (UWB) pulse signal.

FIG. 5 is a block diagram of an exemplary embodiment of a sensor system. The sensor system 52 includes various components for controlling, generating, receiving, and processing signals that are dispersed in accordance with the teachings herein. As an exemplary embodiment, a system controller and processor 58 is coupled to a signal generator 62. The controller/processor 58 can control the generator 62 by sending initiation control signals 60 to the generator. The generator 62 produces a generator output signal 64 of EM energy for testing the material in question. The EM energy signals can be pulsed signals, such as short duration pulsed signals having an ultra-wide bandwidth, such as shown in FIG. 6, described below. Alternatively, the EM energy signals can be stepped signals that sequentially expose the material being analyzed to each frequency of interest through a sweep mode. The EM energy can have a wide bandwidth, such as created by amplitude, phase, or frequency modulation, or a combination thereof. Elements which support evanescent waves having a wide bandwidth characteristic are also contemplated. In at least one embodiment, the generator 62 can generate a repetitive sequence of UWB pulses, discussed herein.

Figure 8A:
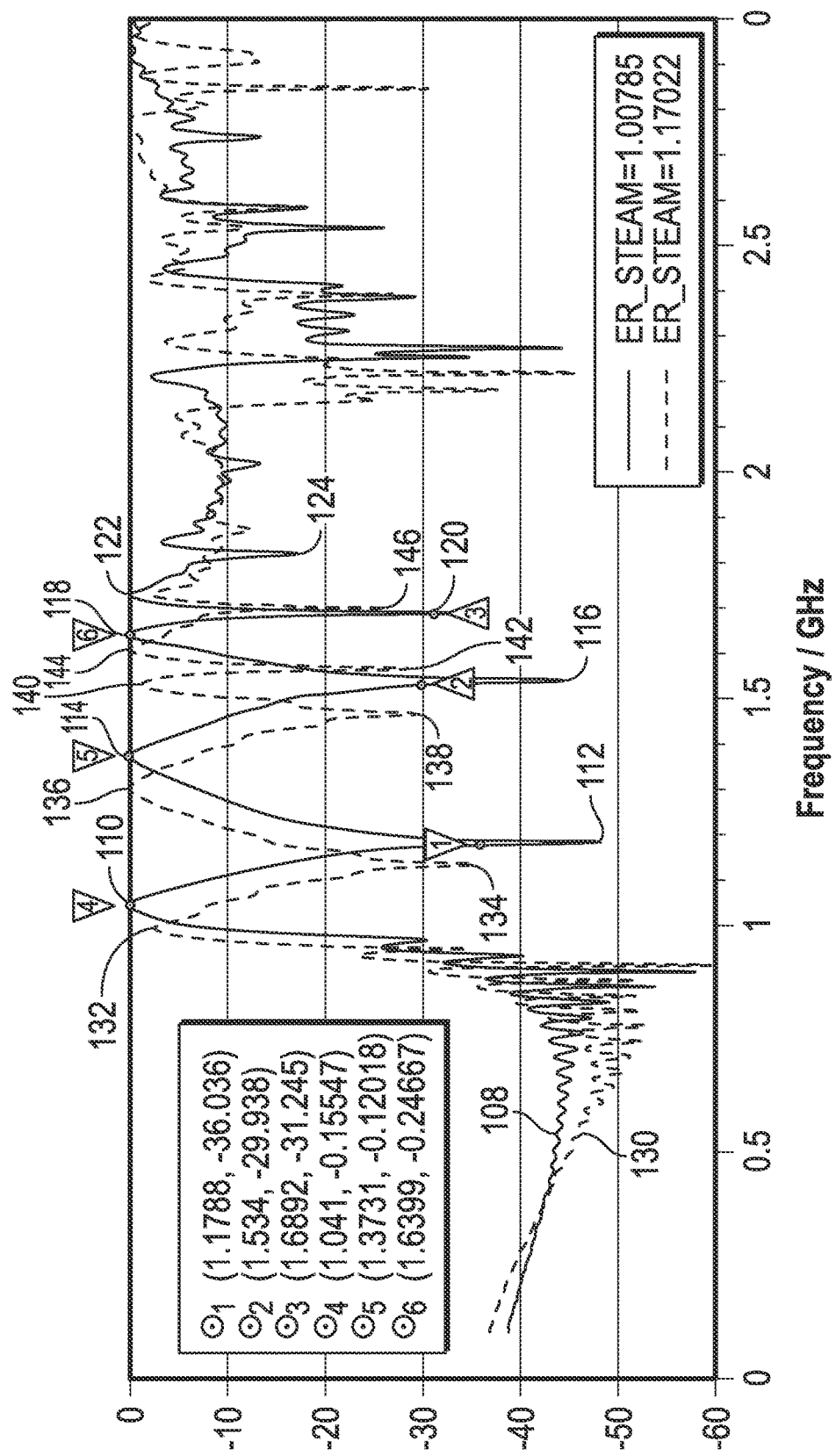
FIG. 8A is a frequency domain representation that could be produced by a UWB pulse input signal.
Figure 8B:
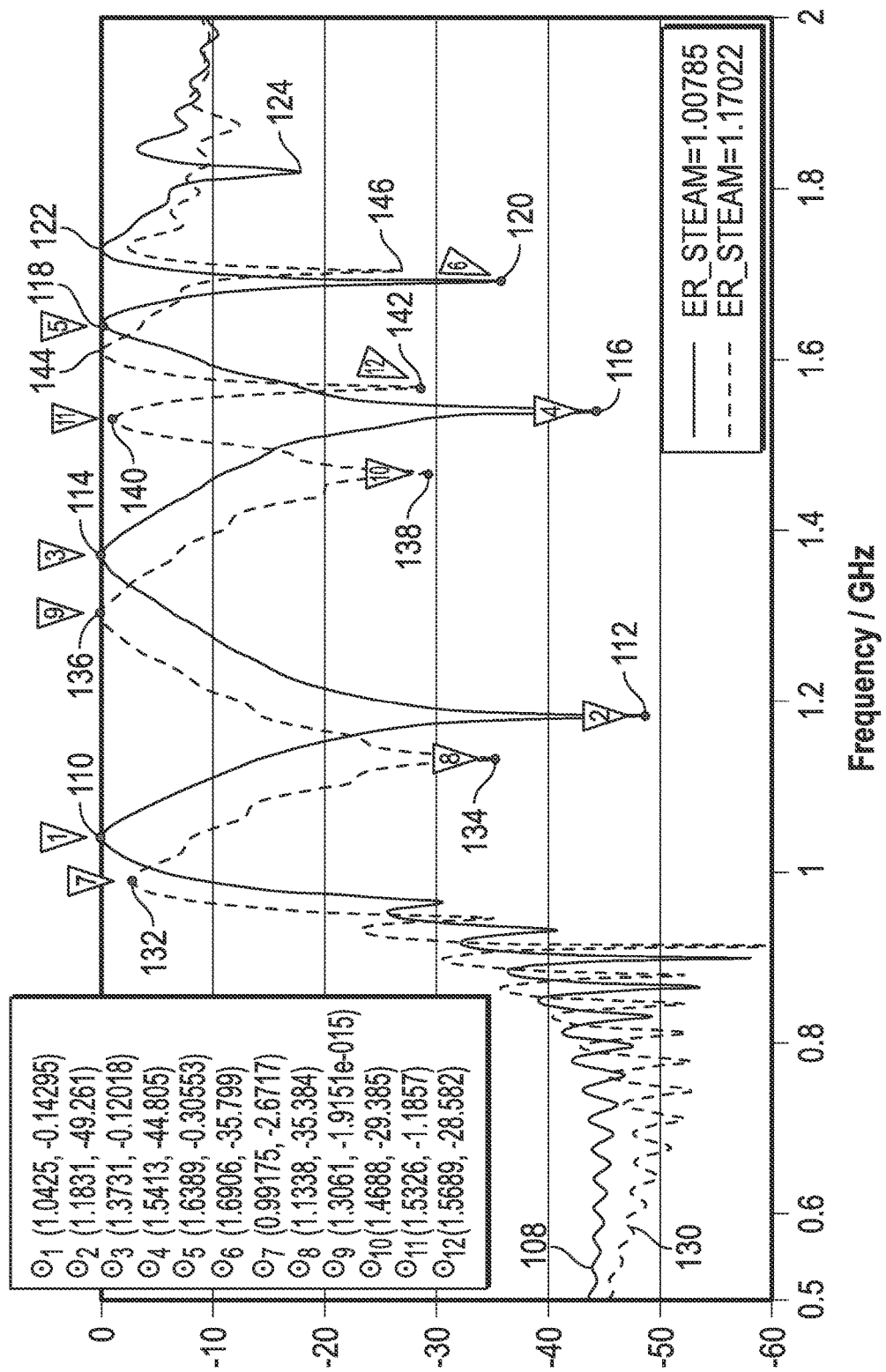
FIG. 8B is a frequency domain representation of an enlarged portion of the output signal of FIG. 8A.
Figure 9:
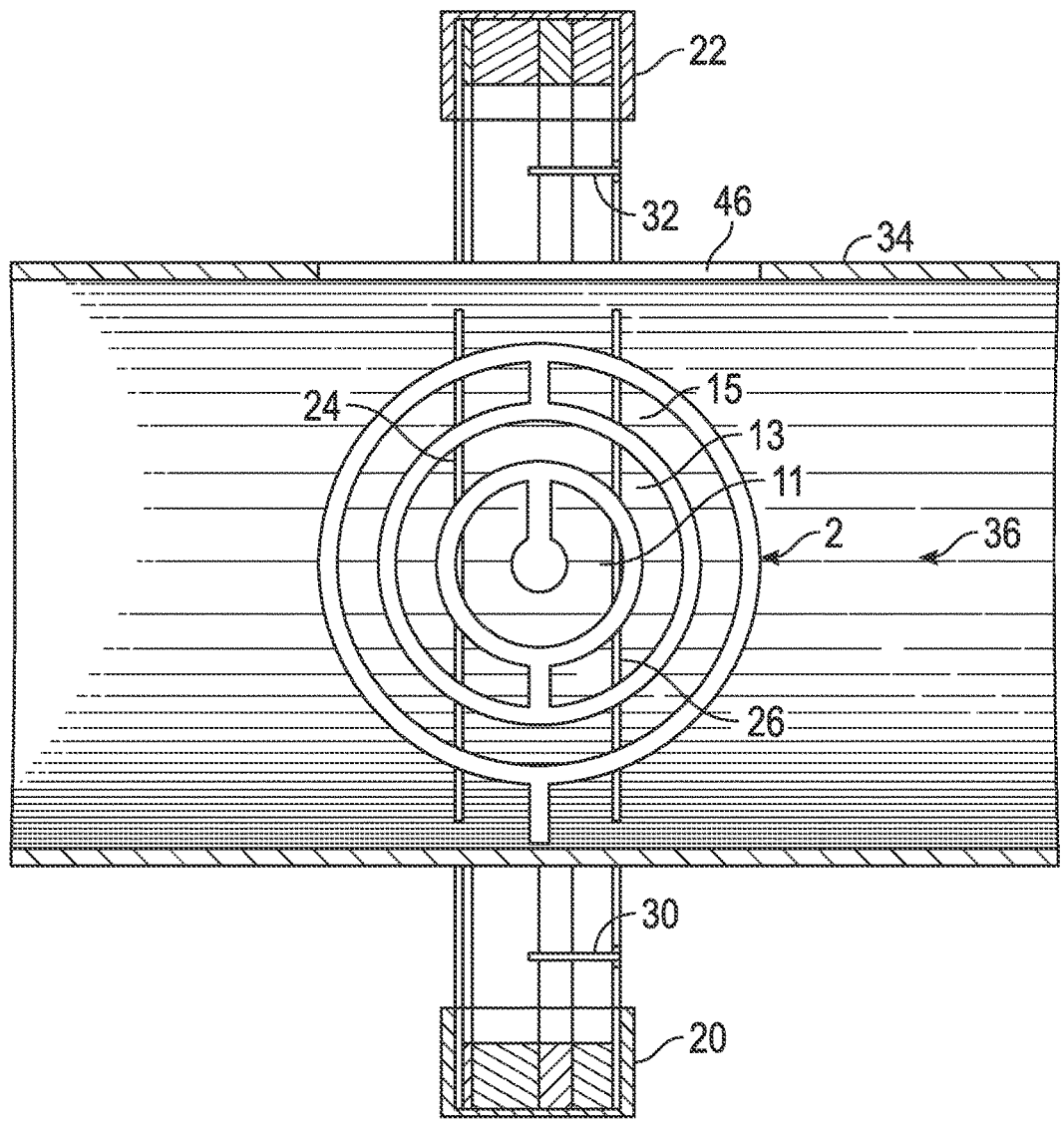
FIG. 9 is a schematic side view of another exemplary embodiment of a steam energy sensor according to the present invention.

The generator 62 is coupled to an input switch 66, and the input switch 66 is coupled to the wave launching structure 30 of the steam quality sensor 2. The generator output signal 64 thus is able to be communicated through the input switch 66 to the sensor 2. The switch 66 can be used to switch between sending a signal to the sensor 2 for dispersion by a material 74 flowing through the flow path 36 and sending a signal from a reference line 70 to an output switch 82. The signal from the reference line 70 can be used for normalization and processing after dispersion of the transmitted signal through the sensor 2, as described below. The function of the input switch 66 can alternatively be accomplished by a power divider circuit. The sensor 2 is selectively coupled through EM energy with the material 74 (such as steam) flowing through the flow path 36. Due to electrical conductivity/permittivity or magnetic conductivity/permittivity of the material 74 in the flow path, the material 74 can alter the transmitted signal of EM energy passing through the sensor 2 from the wave launching structure 30 to the wave receiving structure 32. For example, if the generator 62 produces pulses to the wave launching structure 30, then the signals received by the wave receiving structure 32 will be dispersed pulses, such as shown in FIGS. 8A, 8B, and 9, described below.

The wave receiving structure 32 is coupled to an output switch 82, and to which the wave receiving structure 32 can forward a receiver output signal 80, resulting from the signal dispersion through the sensor 2 caused by the material 74 in the flow path 36. The output switch 82 is coupled to a receiver 86. The receiver 86 is coupled to the system controller and processor 58, referenced above. The dispersed signals received by the wave receiving structure 32 are able to be communicated through the output switch 82 to the receiver 86. The function of the output switch 82 can alternatively be accomplished by a power combiner circuit and is included as an equivalent. If the receiver 86 uses equivalent time sampling methodology, then the receiver 86 can sample the sensor output having the response dispersed signals to produce acquired sample representations.

The functions performed by controller and processor 58 also comprise system-timing operations, including sending initiation control signals 60 to the generator 62, generating switch control signals 92 for control of input switch 66 and output switch 86, receiver sampling control 90 for control of sample timing in the receiver 86, as well as synchronization and interactive system and visual display control.

In at least one embodiment, the signals received by the receiver 86 can be time-sampled to convert the output to a digital format that can be used by the controller and processor 58. If short UWB pulses are used, then to form an accurate digital representation of a narrow-width pulse would ordinarily require that the pulse be sampled at a very high sampling rate, which requires relatively costly electronics. This high cost can be avoided using an equivalent time-sampling technique. Rather than sample each pulse at a very high rate, each sample that is needed to provide an accurate representation of a pulse can be acquired from a different pulse in the sequence of pulses received after the influence of the material 74. This method allows use of a much slower sampling rate because of the relatively long time duration between pulses. The samples obtained from each pulse are then temporally aggregated to form an acquired sample representation that accurately reproduces a dispersed pulse. This sampling method substantially reduces the cost of the receiver and enables the advantageous use of UWB pulses for material measurements that would otherwise be prohibitively expensive in many applications.

Because the EM energy signals can propagate away from a measurement zone within the vessel 34, unwanted reflections of propagating energy from obstructions exterior to the measurement zone can occur. However, because of the time delay that occurs for propagating energy to exit the vessel, reflect from an obstruction, and return to the wave receiving structure 32 of the sensor 2, this unwanted reflected energy will arrive at a time that is discernibly later than the time of arrival of the energy that is communicated directly through the vessel. The receiver 86 can discriminate between the late-arriving energy and the energy communicated directly through the measurement zone within the vessel. By excluding the late arriving energy from the process, measurement errors arising from unwanted reflections are avoided.

To accurately measure time of arrival and the dispersion caused by the vessel, as well as to distinguish the dispersed pulse from unwanted later-arriving energy, the pulses of at least one embodiment are generally of very short duration, preferably exhibiting a very rapid rise time, and the time duration between successive pulses must be sufficiently long in comparison to the duration of a pulse. In at least one embodiment, the duration of a pulse can be shorter than a nano-second and the pulse repetition frequency is on the order of a few mega-Hertz (MHz).

Further, the system can provide for time-domain gating in receiving and processing the signals, such as UWB pulses. The process of time-gating excludes energy in the received signal that occurs before or after a designated time. This gating can reduce or eliminate sources of error arising from the upstream and downstream reflections of energy from obstructions exterior to the vessel. For example, when the generator 62 produces a repeating sequence of pulses, the time-gate is applied repetitively to exclude unwanted energy arising from each pulse, while accepting the desired energy arising from each pulse. Time gating can also be used to separate a signal from the reference line 70 from the receiver output signal 80. The reference line path can be shorter than the measurement path to permit time separation of the measurement and reference signals.

For those embodiments using pulses for input EM energy, the timing of the pulses can be at a regular spacing according to a fixed pulse repetition frequency. Thus, the time intervals between successive pulses will be substantially equal. Alternatively, a pseudorandom or other non-uniform pulse spacing technique can be used. A non-uniform spacing can be selected that will distribute the various frequency components in the pulse sequence over a broad band of frequencies that will appear as a low level noise spectrum to other electronic equipment that could otherwise be affected by stray emissions from the sensor electronics.

Also, the acquired sample representations may be outputted to an output device 94, such as a video monitor, printer, voice synthesizer, or other sensory output devices to obtain information concerning properties of the substance. For example, the output device 94 may show the amplitude and shape of the received output as a function of time. A time lag between the time when an input energy is transmitted and the time when the output energy is received is caused by the time duration of propagation of the input energy interacting with the material. This time delay can be visually observed and employed to infer properties of the substance. Further, the material 74 interacting with the input energy may cause an attenuation of energy amplitude that can also be visually observed. Moreover, the substance interacting with the energy may cause dispersion of the energy, thereby causing a visibly observable distortion of the shape of the output energy.

Figure 7:
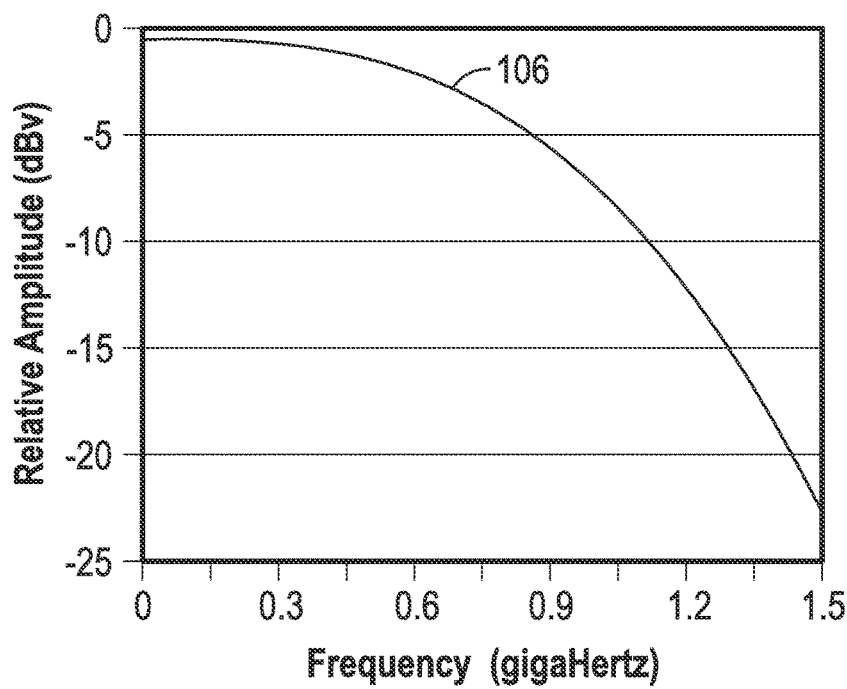
FIG. 7 is the frequency domain representation of the pulse in FIG. 6.

An output signal can be visually displayed and analyzed in either the time domain or frequency domain. As is known, a signal that varies as a function of time may be represented by a unique signal that varies as a function of frequency. Either representation contains equivalent information. They are mathematically related by a Fourier Transform integral. This integral resolves a continuous-time signal into a continuous-frequency spectrum. Thus, in the alternative to time-domain analysis, it may be convenient to convert the output equivalent-time sampled pulse signal to the frequency domain. The acquired sample representation may be converted to a frequency-domain representation using a Fast Fourier Transform (FFT) algorithm prior to further analysis. The FFT resolves the acquired sample representation into a discrete frequency spectrum. An example is shown in FIGS. 6 and 7 herein and described below.

Further, although applying a Fourier Transform to the output signal enables display and analysis in the frequency domain, other transformations may be applied to the signal captured by the receiver 86 to cause other attributes of the signal to be exhibited and analyzed. For example, certain frequency components may be weighted more heavily due to a priori knowledge concerning a desired frequency response of the substance. Likewise, the acquired signal may be time-weighted to emphasize certain temporal features of the signal. As another example, the acquired signal, after being transformed to the frequency domain may be processed by digital filtering before further analysis. Also, the signal can simply be integrated or differentiated prior to or after one or more other transformations are applied. Thus, more generally, the response signal may be processed by performing a transformation of the response signal to produce a resultant signal that is a function of a variable of the transformation.

The signal processing of the acquired sample representation obtained in the receiver 86 can be performed by the controller and processor 58. Further, the controller and processor 58 can use decision algorithms to predict values for the parameter variables of interest. As will be understood to those in the field, controller and processor 58 may include a microprocessor operating under the directions of software that implements the desired algorithms and other functions.

It will often be useful to normalize the spectrum of the receiver output signals 80 by the spectrum of the generator output signals 64. The normalization process has the benefit of removing unit-to-unit variations in both the amplitude of the transmitted signals and the gain and frequency response characteristics of the receiver 86. To accomplish the normalization, an attenuated sample of the input signal may be applied directly to the input of the receiver 86 through the signal from the reference line 70. An input to the reference line 70 can be communicated through the switch 66 that is coupled to the reference line. An output from the reference line 70 can be communicated through the switch 82 that is coupled to the reference line. The receiver 86 and/or system controller and processor 58 can then reproduce an input signal to the sensor 2 and convert the input signal and sensor output to common units for normalization. In at least one embodiment, the input and output of the sensor can be converted from a time domain representation to a frequency domain representation through a Fourier Transform, such as an FFT, to produce a spectral representation of that input signal to the sensor and the output signal from the sensor. When the signals are converted to decibels (dB), normalization involves simple subtraction operations between the input signal and the output signal.

As another example of a system for the sensor, the output device 94 can be portably coupled with the sensor 2. An indicator on the device 94 can indicate whether sufficient data is gathered to provide a measurement of the intended condition(s) or whether another attempt is required. Based on an analysis conducted on sufficient data, such as described above, a display on the device can indicate one or more conditions that are being measured, such an analog or digital readout of a numerical value, a sequence of various lights, various colored-coded lights, or other visual indicators of the one or more conditions. In addition to or substitution of one or more visual outputs, in some embodiments, the output device 94 may provide other output, such as audible, tactile, or other sensory output. The output device 94 can be an alarm indication consisting of a blinking light, a buzzer or similar indication to communicate to a user that a predetermined condition of the material under test has been reached or exceeded, requiring some response on the part of the user. The output device may include capabilities for transmission, such as Bluetooth® technology, infrared, and other wireless or wired transmission means. The transmission can be coupled with a computer, monitoring system, pager, or other devices that, for example, can alert third parties of an adverse or other sensed condition.

FIG. 6 is a graphical representation of an exemplary ultra-wide band (UWB) pulse signal. FIG. 7 is the frequency domain representation of the pulse in FIG. 6. The figures will be described in conjunction with each other. The particular pulse shown in FIG. 6 is a Gaussian amplitude-weighted sin(x) over x pulse, representative of a general class of UWB pulses, but not the only type of pulse that may be employed in the present invention. The frequency of the UWB signal can be shifted up and down in range for optimization of the signal that is received by the receiver. For example, a carrier can modulate the frequency to shift to a different portion of the electromagnetic spectrum. (Note that in FIG. 6, both negative and positive values appear along the horizontal axes as shown, with time t=0 coinciding with the peak of the pulse. This is consistent with standard mathematical analysis methods, although other coordinate orientations can be employed.) In at least one embodiment, the generator 62, shown in FIG. 5, can produce a series of short duration pulses. An inverse relationship exists between the time duration of a pulse of energy and the frequency bandwidth of the energy spectrum of the pulse. The shorter the duration of the pulse, the wider will be the band of frequencies of energy comprising the pulse.

The bandwidth of such pulses can be approximated according to the following equation:

$$BW = \frac{.35}{t_r}$$

where BW is the bandwidth of the pulsed signal in Hertz and $t_r$ is the rise or fall time of the signal in seconds. For example, rise or fall times on the order of 100 ps will produce an approximate signal bandwidth of 3.5 GHz.

Therefore, the frequency spectrum of a narrow input pulse, such as is shown in FIG. 6, will resemble the broad spectrum shown in FIG. 7. A sufficiently narrow UWB pulse 104 will exhibit a broad frequency domain 106 of energy that interacts over a desired frequency range for dispersion of the signal due to interaction with the material 74 in the flow path 36, shown in FIG. 5. This dispersion can be a function of frequency, the shape and size of the flow path, and the characteristics of the material.

Dispersion affects the shape, duration, phase, and time of arrival of the energy pulses as output signals from the sensor, where the dispersed pulses are received by the receiver 86 in FIG. 5. Thus, the input signal becomes dispersed with one or more frequency responses of substantial amplitude over a broad spectrum.

FIG. 8A is a frequency domain representation that could be produced by a UWB pulse input signal. FIG. 8B is a frequency domain representation of an enlarged portion of the output signal of FIG. 8A. The figures will be described in conjunction with each other. The signals 108, 130 described below are illustrative of a signal generated through the embodiment of the steam quality sensor 2 that is shown in FIG. 2. A signal 108 represent 100% vapor and would be considered a "dry" steam. The signal is transformed into a frequency domain as described above to help facilitate analysis of the peaks and nulls of various frequencies. For example, at lower frequencies represented generally to the left of a first peak 110, the frequencies are not substantially if at all propagating and fall below a cut-off frequency for the signal through the dispersive medium affected by the flowing steam. The first peak 110 occurs at a frequency in this example of about 1.05 GHz with a corresponding first null 112 at about 1.19 GHz. This first peak and first null generally would occur at the resonator 17 described in referenced to FIGS. 1-4. This signal further has a second peak 114 at about 1.38 GHz followed by a second null 116 at about 1.53 GHz. The second peak and second null will correspond generally to the resonator 15. This signal further has a third peak 118 at about 1.64 GHz followed by a third null 120 at about 1.68 GHz. The third peak and third null will correspond generally to the resonator 13. This signal further has a fourth peak 122 at about 1.73 GHz followed by a fourth null 124 at about 1.82 GHz. The fourth peak and fourth null will correspond generally to the resonator 11. The remainder of the signal is shown and would contain further information in a likewise manner depending on the number of resonators. At higher frequencies, the flow path itself may begin to propagate the signal and thus require further processing to capture relevant data.

A further exemplary signal 130 is shown in FIGS. 8A-8B that is transmitted between the transmitter and the receiver for a 30% steam quality. Other values for steam quality can be and are fully expected to be used, and thus the two examples are only exemplary of underlying concepts of the shift in frequencies depending upon the steam quality. The steam quality can vary from 0% (100% water) to 100% (0% water) and any increment between, and often a desirable steam quality is between 30% to 90% in commercial uses. The resonant frequency of the flow sensor is controlled by the electrical permittivity of the steam that flows through the sensor 2. The sensor 2 can be used to determine the steam quality and variations by measuring the shift in at least one of the resonators' responses. The signal 130 shows a shift to the left at lower frequencies due to the relatively "wet" steam compared to the response of the signal 108 for the relatively "dry" steam. More specifically, the first peak 132 of the signal 130 is at about 1.0 GHz with the first null 134 at about 1.13 GHz for the resonator 17. A second peak 136 for the signal 130 is shown at 1.3 GHz followed by a second null 138 at about 1.47 GHz for the resonator 15. A third peak 140 is at about 1.53 GHz followed by a third null 142 at about 1.56 GHz for the resonator 13. A fourth peak 144 is at about 1.62 GHz followed by a fourth null 146 at about 1.6 GHz for the resonator 11. Further peaks and nulls are shown in the graph in FIGS. 8A-8B.

FIGS. 9-16 illustrate further non-limiting exemplary embodiments of a sensor according to the teachings herein. While the text and figures generally describe exemplary embodiments in the context of an open vessel having a flow path, it is understood that the sensor embodiments can be mounted is a closed vessel to establish the steam energy, such as steam quality, but may not apply the ability to obtain measurements of a flow that would occur through a flow path.

Figure 10:
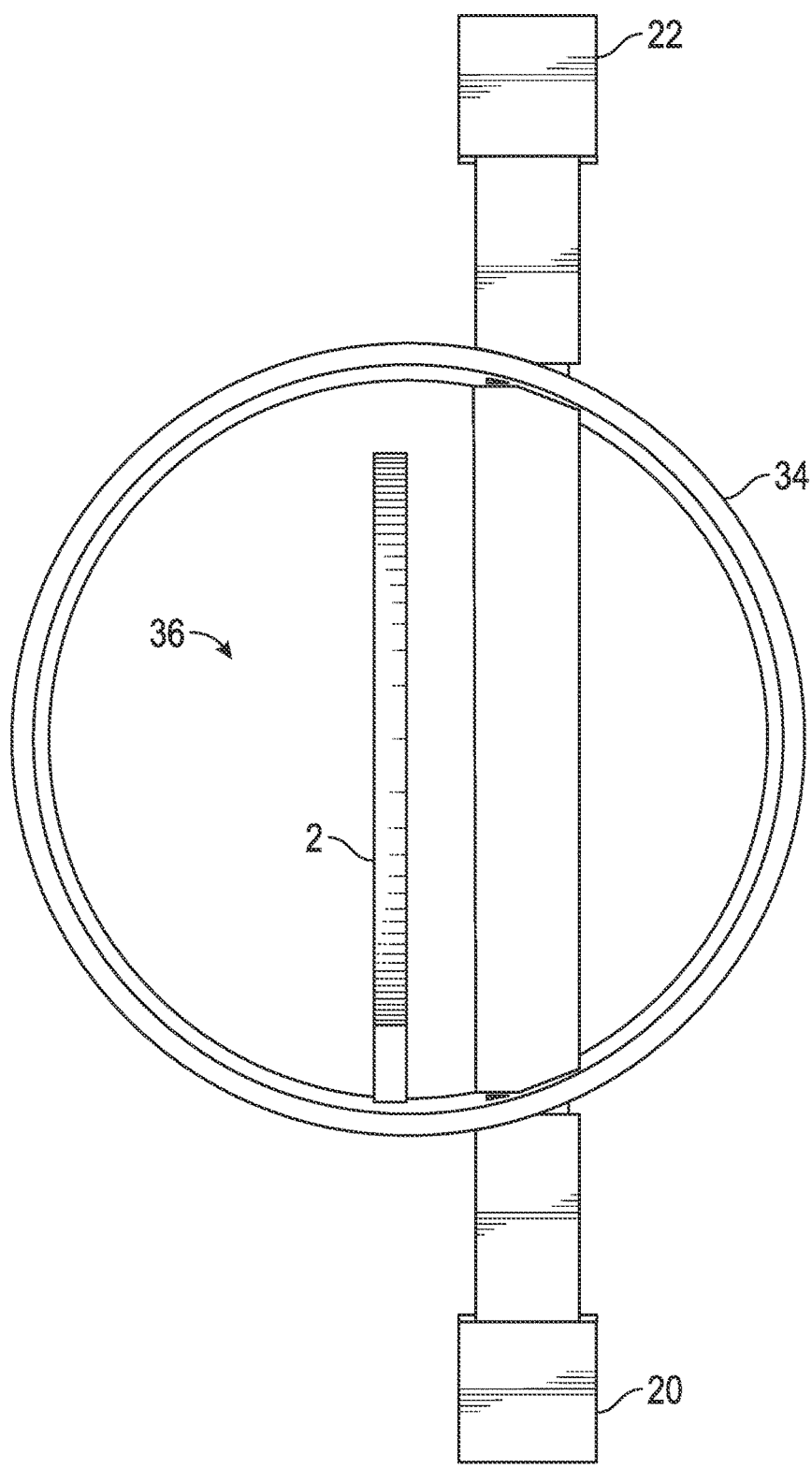
FIG. 10 is a schematic end view of the exemplary embodiment of the steam energy sensor of FIG. 9.

FIG. 9 is a schematic side view of another exemplary embodiment of a steam energy sensor according to the present invention. FIG. 10 is a schematic end view of the exemplary embodiment of the steam energy sensor of FIG. 9. The figures will be described in conjunction with each other. The sensor 2 can be inserted through an opening 46 in the vessel 34. When the vessel 34 has a flow path 36, the sensor 2 can be oriented generally in line (parallel) to the flow path 36 rather than generally transverse as shown in FIGS. 1-4. The sensor would therefore primarily function as a steam energy sensor, such as for steam quality, and not as a flow sensor using orifice principles. The wave launching structure 30 with the transmitter housing 20 and the wave receiving structure 32 with the receiver housing, such as described in FIG. 2 (with alternatives being as described in FIG. 4 and other variations), can be placed at least partially inside the vessel 34 to introduce a wave into the vessel for the sensor 2 to measure the effects caused by the fluid in the vessel.

Figure 11:
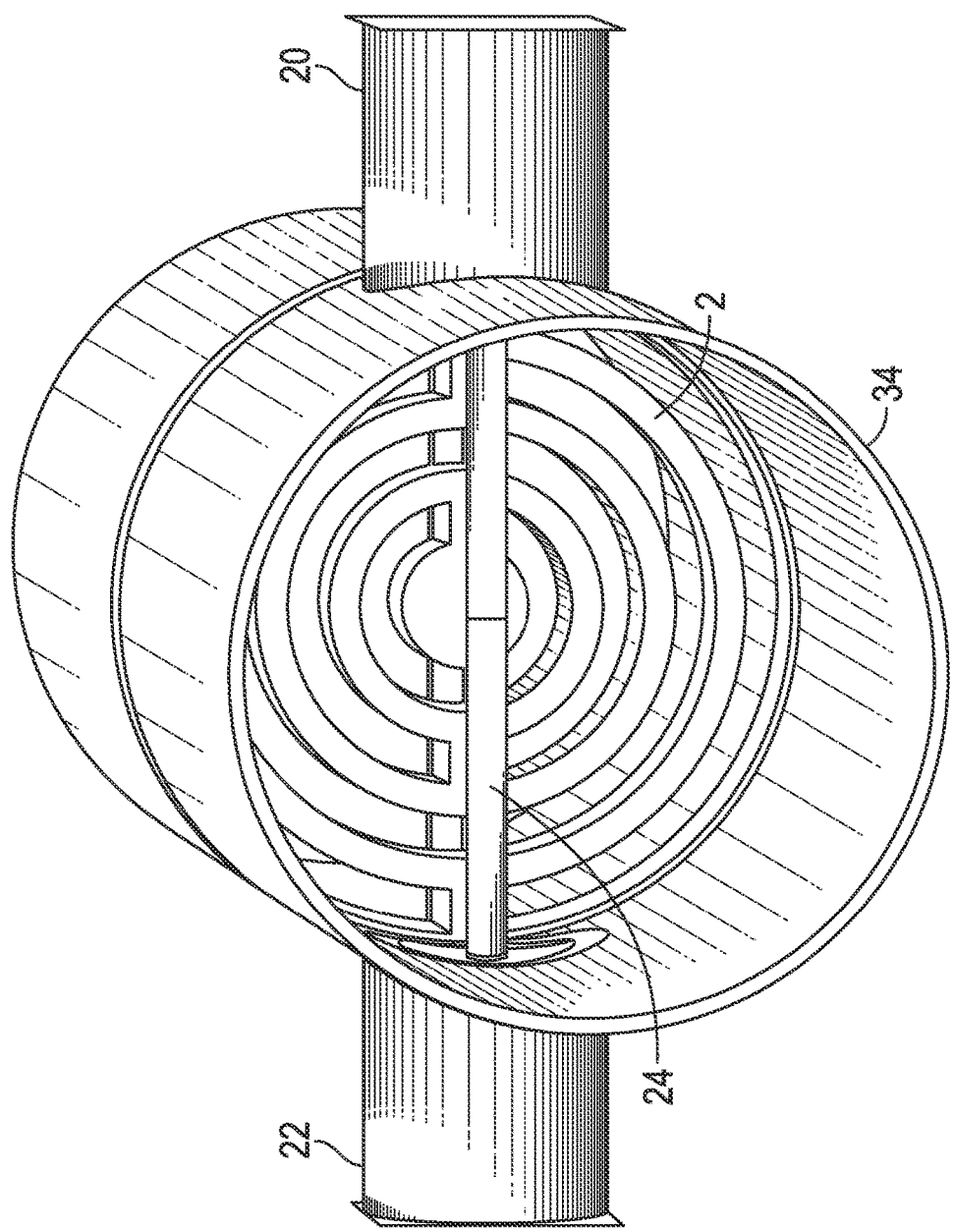
FIG. 11 is a schematic perspective view of another exemplary embodiment of a steam energy sensor according to the present invention.

FIG. 11 is a schematic perspective view of another exemplary embodiment of a steam energy sensor according to the present invention. A sensor 2, as described above, can be inserted into the vessel 34 transverse to a flow path through the vessel 34. A transmitter housing 20 and a receiver housing 22 can include hardware to couple to a wave guide 24, represented as a rod but could be a variety of shapes, to introduce a wave through the wave guide 24 into the vessel in conjunction with the sensor 2. The coupling to the guide 24 in this embodiment does not need the exemplary probes as a wave lunching structure and a wave receiving structure described above. In this embodiment, the wave energy is between the guide 24 and the sensor 2, rather than between two parallel plates as described above.

Figure 12:
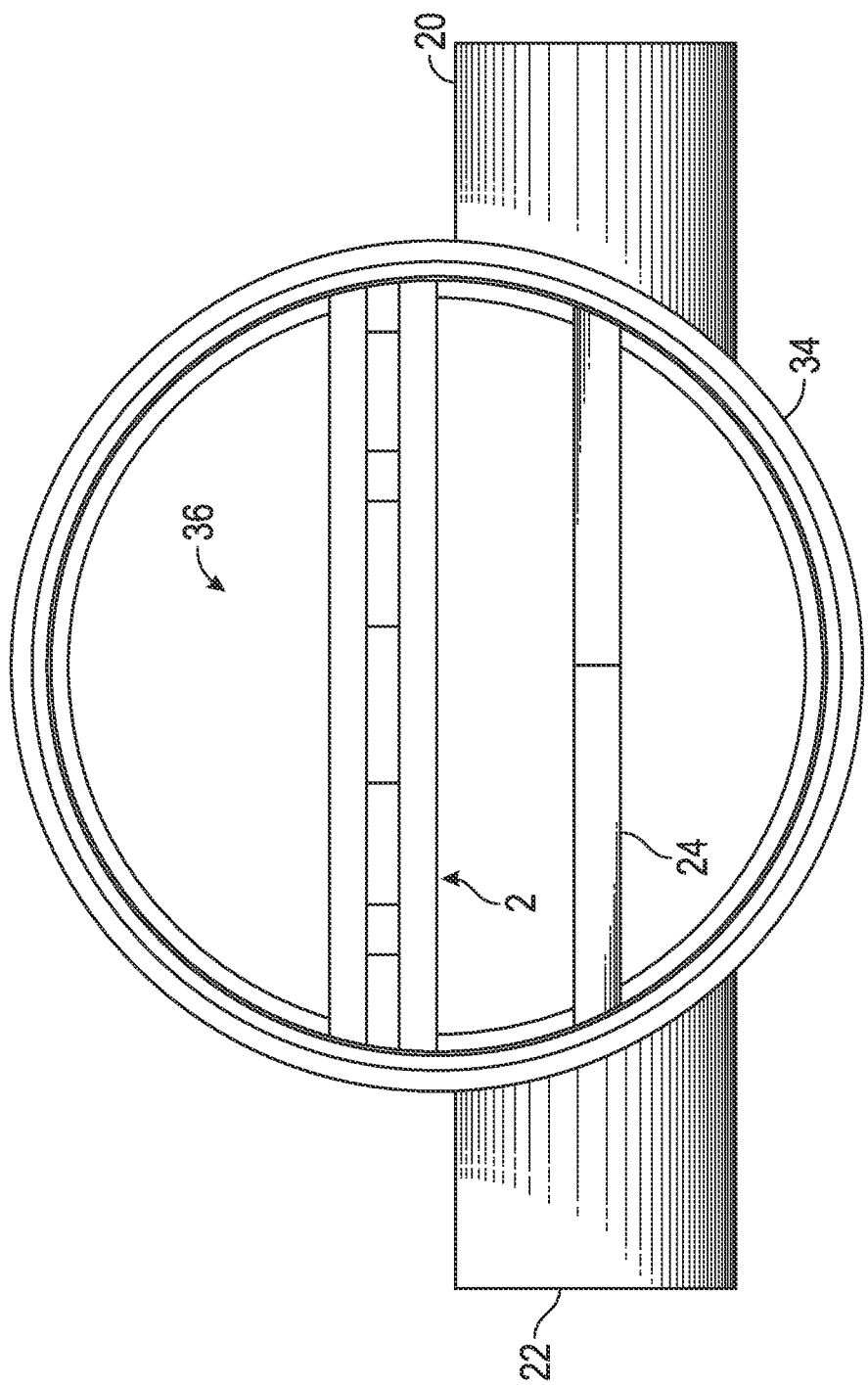
FIG. 12 is a schematic end view of another exemplary embodiment of a steam energy sensor according to the present invention.
Figure 13:
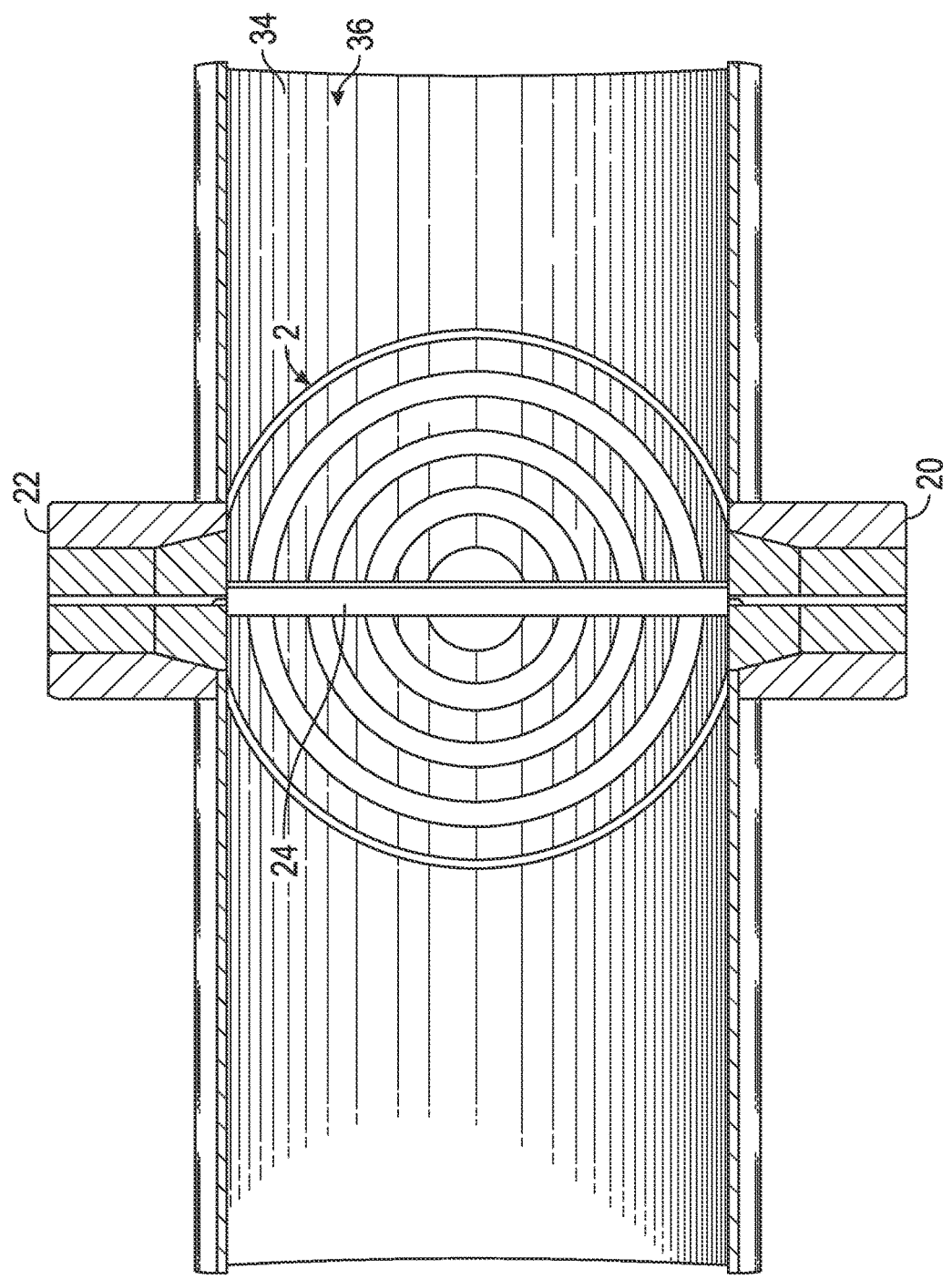
FIG. 13 is a schematic side view of the exemplary embodiment of the steam energy sensor of FIG. 12.

FIG. 12 is a schematic end view of another exemplary embodiment of a steam energy sensor according to the present invention. FIG. 13 is a schematic side view of the exemplary embodiment of the steam energy sensor of FIG. 12. The figures will be described in conjunction with each other. This embodiment is similar to the embodiment shown in FIG. 11, except that the sensor 2 is mounted in-line with a flow path 36 through the vessel 34. The transmitter housing 20 and receiver housing 22 with associated equipment described above can introduce a wave through the wave guide 24 that is mounted into the flow path.

Figure 14:
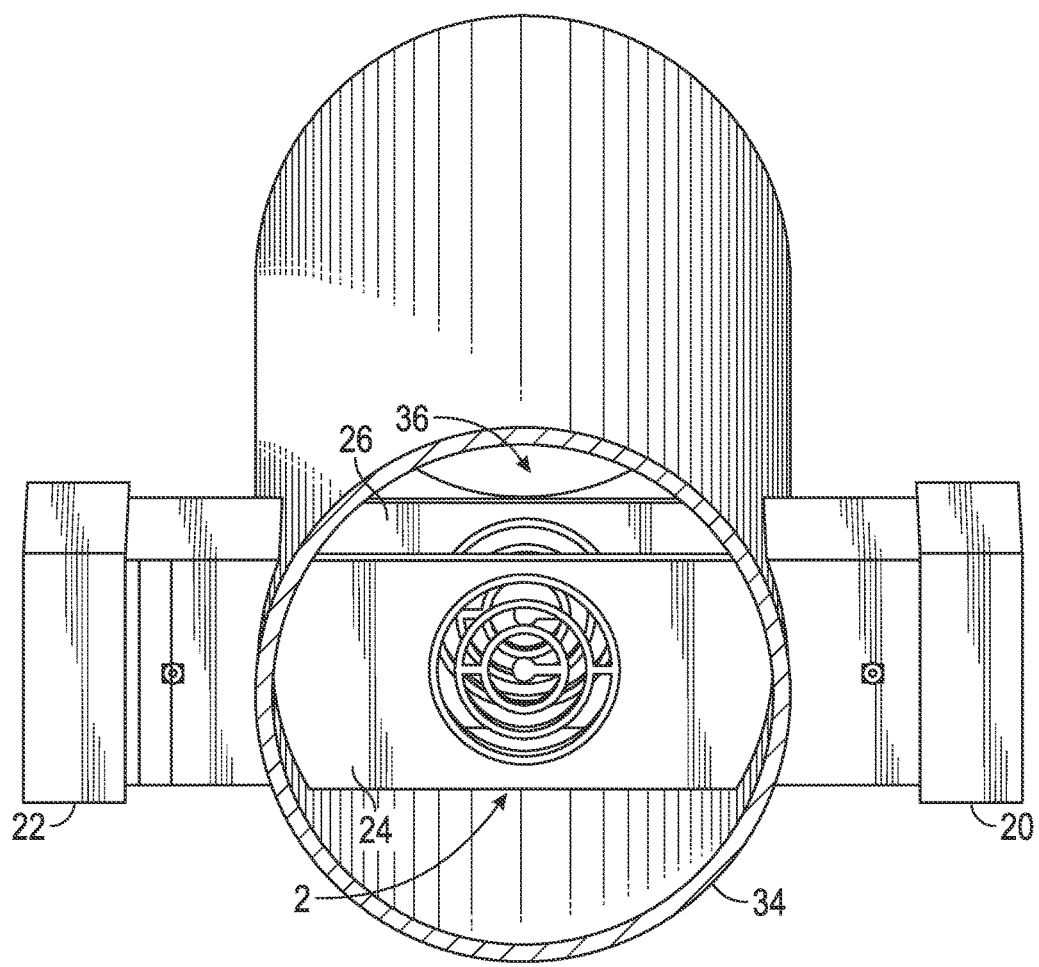
FIG. 14 is a schematic perspective view of another exemplary embodiment of a steam energy sensor according to the present invention.

FIG. 14 is a schematic perspective view of another exemplary embodiment of a steam energy sensor according to the present invention. One or more sensors 2 are incorporated into the structure of the wave guide 24 and/or the wave guide 26. The wave guides 24 and 26 and sensor(s) 2 can be transversely mounted into the flow path 36 of the vessel 34, so that the fluid in the flow path flows through the openings in the sensor(s) 2 described above and around the wave guides 24 and 26. The transmitter housing 20 and receiver housing 22 can include the equipment useful for introducing a wave in the wave guides, generally so that the wave energy is between the wave guides.

Figure 15:
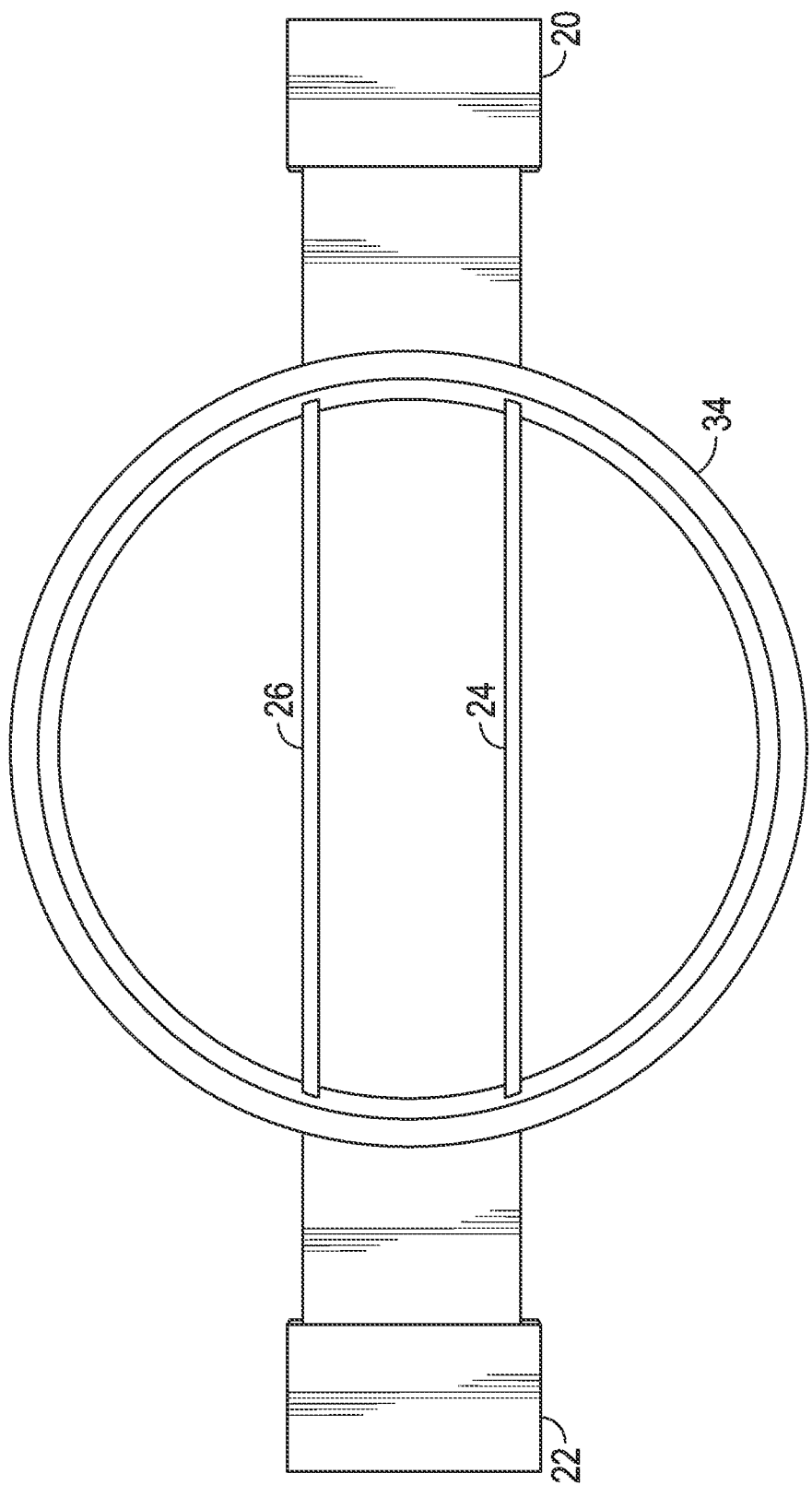
FIG. 15 is a schematic end view of another exemplary embodiment of a steam energy sensor according to the present invention.
Figure 16:
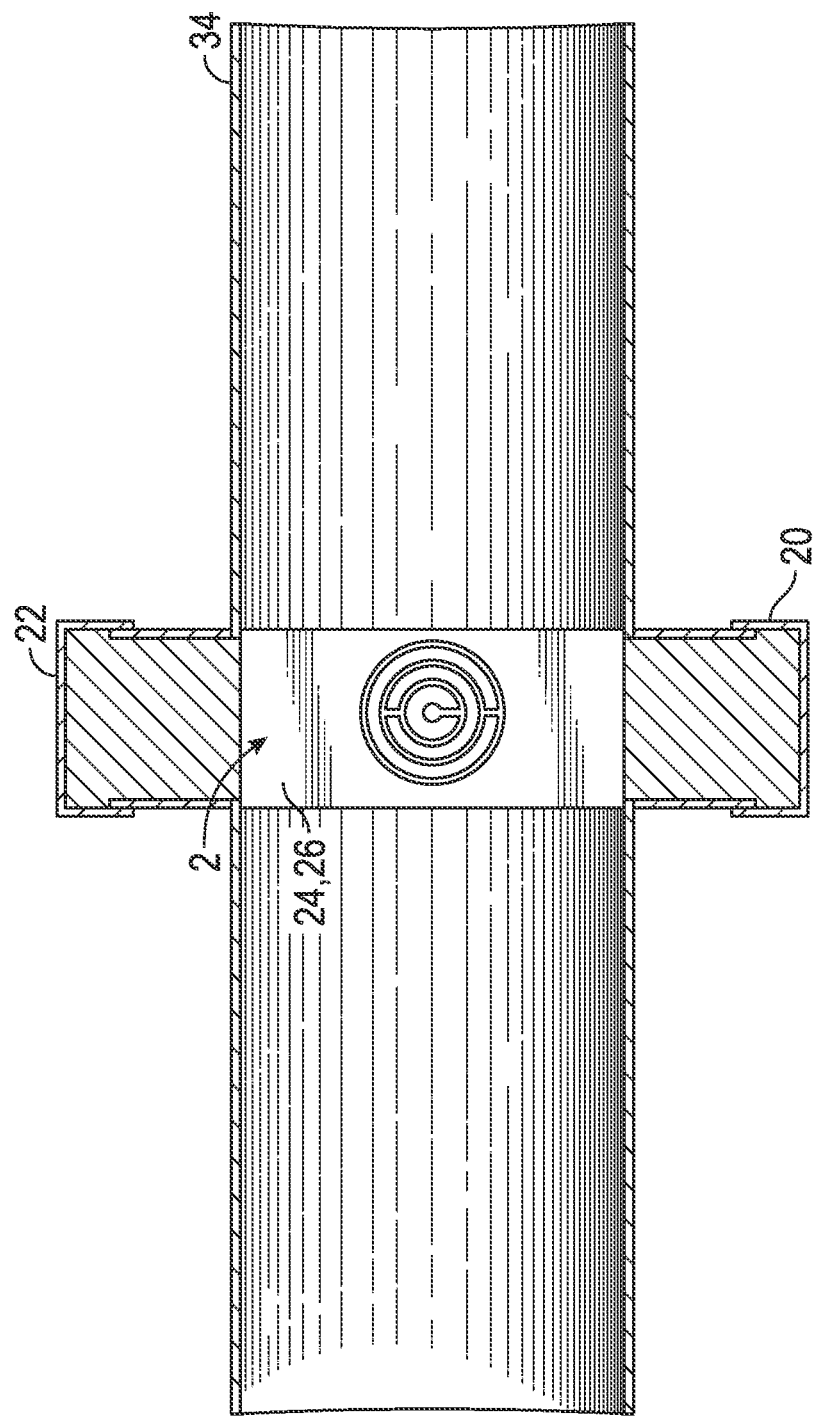
FIG. 16 is a schematic side view of the exemplary embodiment of the steam energy sensor of FIG. 15.

FIG. 15 is a schematic end view of another exemplary embodiment of a steam energy sensor according to the present invention. FIG. 16 is a schematic side view of the exemplary embodiment of the steam energy sensor of FIG. 15. The figures will be described in conjunction with each other. One or more sensors 2 are incorporated into the structure of the wave guides 24 and/or 26. The wave guides 24 and 26 and the one or more sensors 2 can be mounted in-line with the flow path 36 of the vessel 34. The transmitter housing 20 and receiver housing 22 can include the equipment useful for introducing a wave in the wave guides 24 and 26.

Figure 17A:
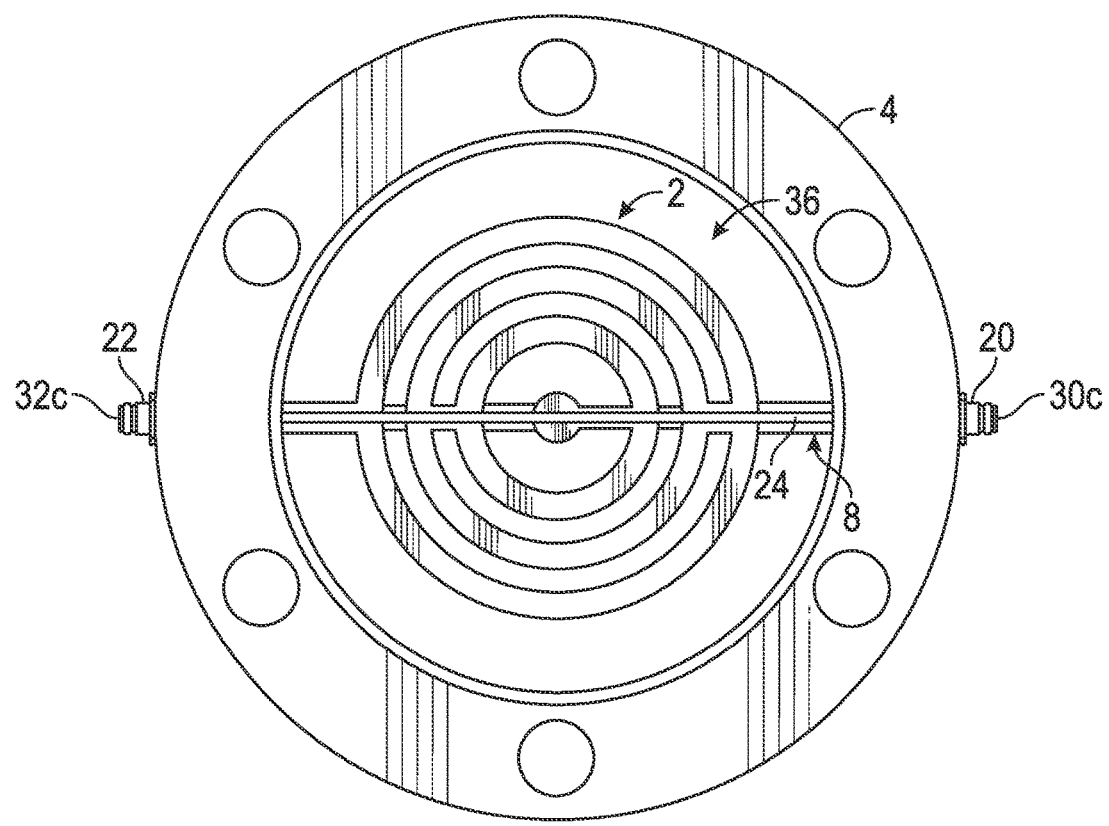
FIG. 17A is a schematic front view of another exemplary embodiment of a steam energy sensor according to the present invention.
Figure 17B:
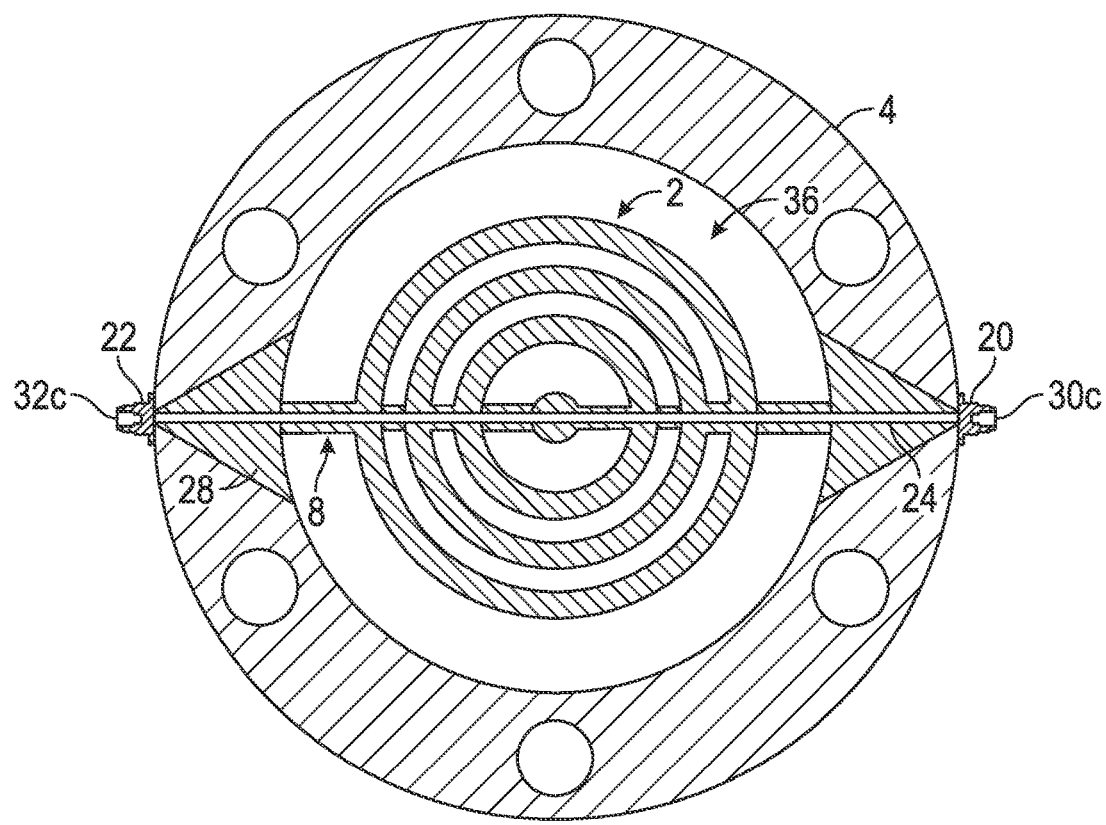
FIG. 17B is a schematic cross-sectional view of the exemplary embodiment of the steam energy sensor of FIG. 17A.
Figure 18:
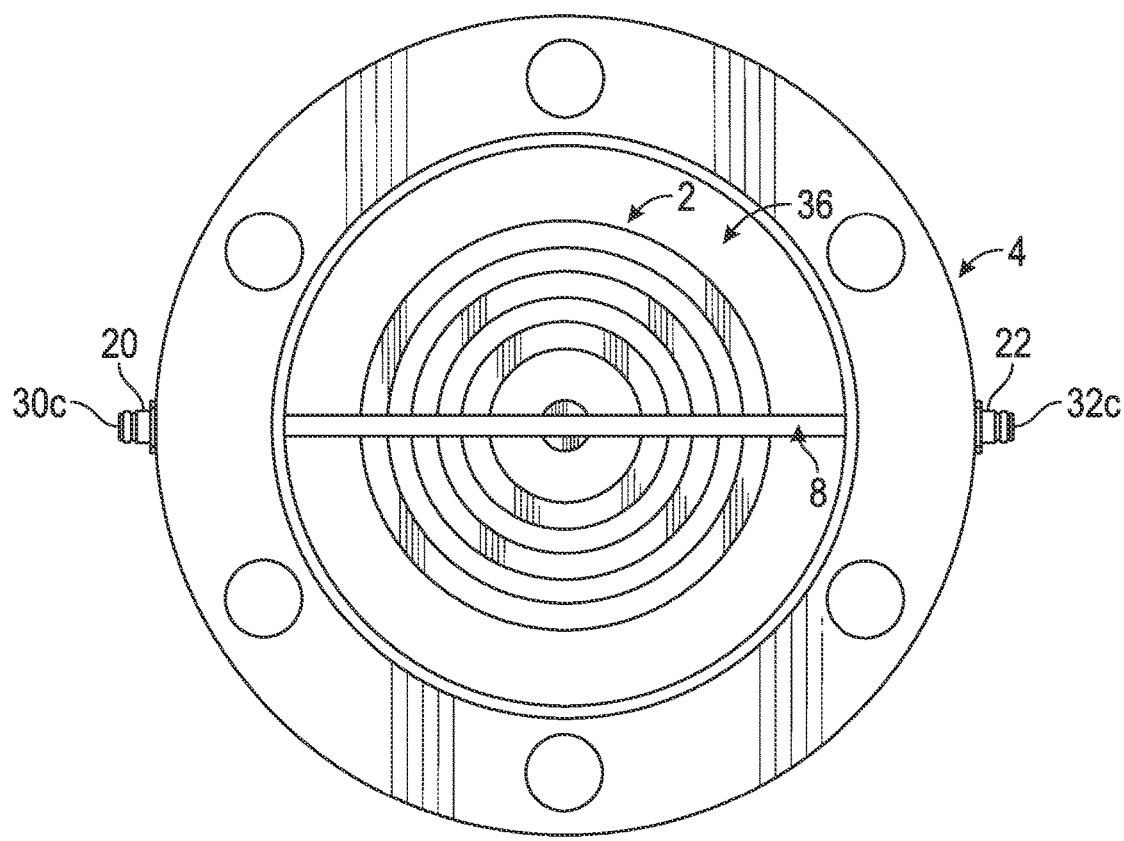
FIG. 18 is a schematic rear view of the exemplary embodiment of the steam energy sensor of FIG. 17A.

FIG. 17A is a schematic front view of another exemplary embodiment of a steam energy sensor according to the present invention. FIG. 17B is a schematic cross-sectional view of the exemplary embodiment of the steam energy sensor of FIG. 17A. FIG. 18 is a schematic rear view of the exemplary embodiment of the steam energy sensor of FIG. 17A. The figures will described in conjunction with each other.

A fluid energy sensor flow sensor such as a steam energy sensor and more specifically such as a steam quality sensor 2 includes a transmitter housing 20 with a wave launching structure 30C and a receiver housing 22 with a wave receiving structure 32C. A seal 24 can be inserted into a matching cavity into the structure of the sensor 2 to withstand pressure in a flow path 36. A series of split rings, dividers, and stiffeners have been described in the above several figures (not labelled in these figures) is supported by support 8 and disposed in the flow path 36 to measure the energy of flow through the path. One or more wave guides 24 is disposed across the flow path and coupled between the wave launching structure 30C and the wave receiving structure 32C.

Figure 19:
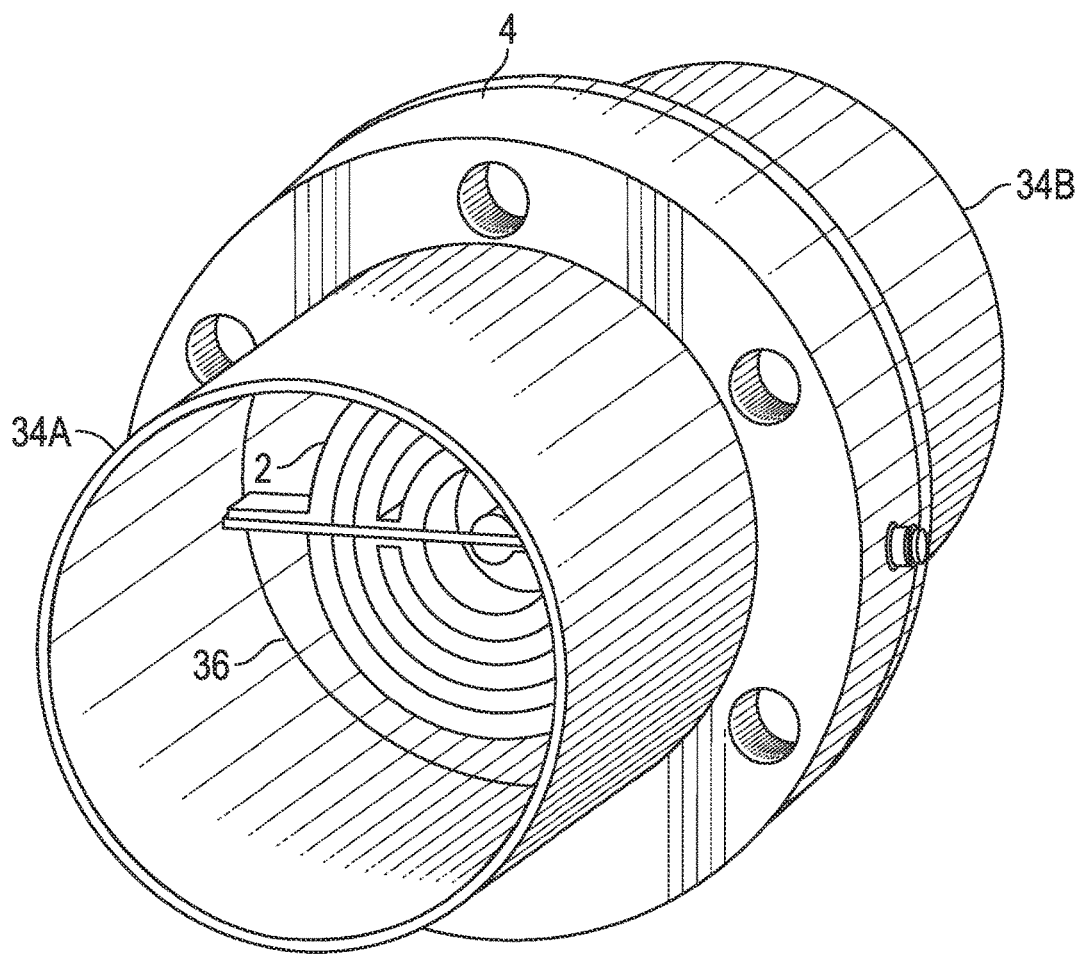
FIG. 19 is a schematic perspective view of the exemplary embodiment of the steam energy sensor of FIG. 17A coupled with a vessel.
Figure 20:
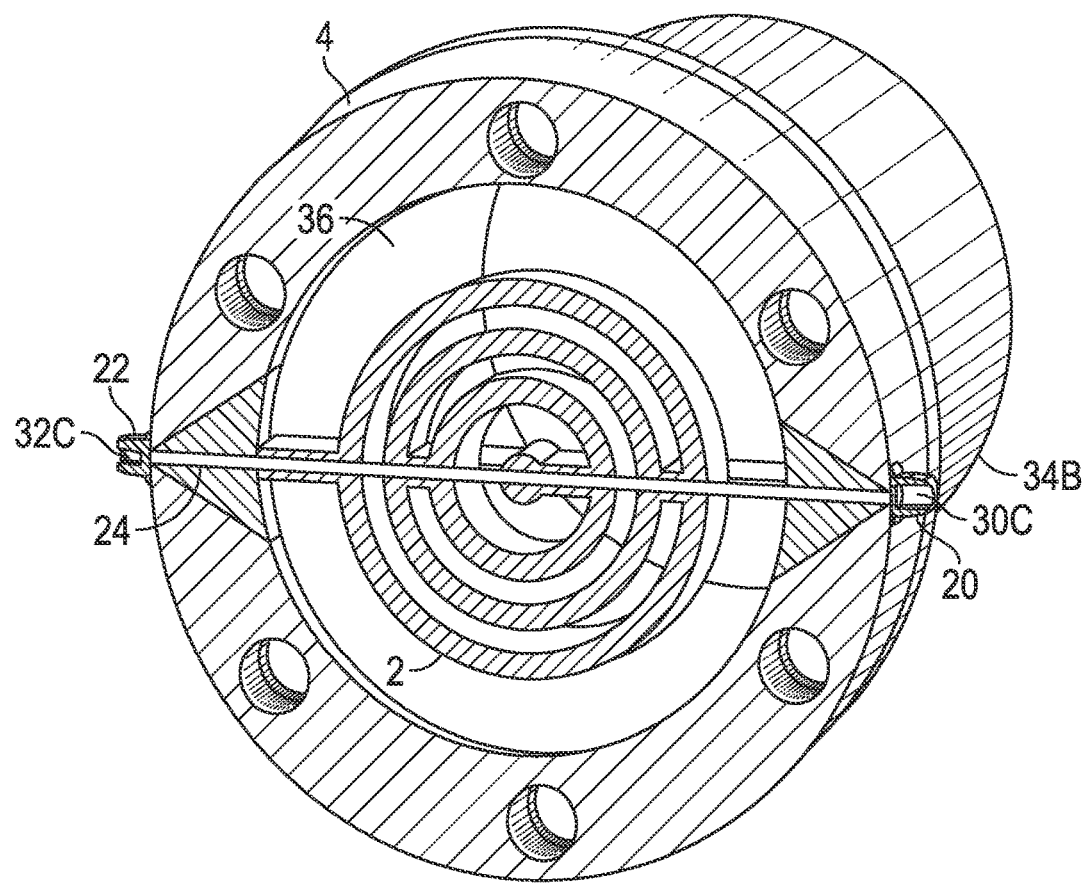
FIG. 20 is a schematic perspective cross-sectional view of the exemplary embodiment of the steam energy sensor of FIG. 17B coupled with the vessel.

FIG. 19 is a schematic perspective view of the exemplary embodiment of the steam energy sensor of FIG. 17A coupled with a vessel. FIG. 20 is a schematic perspective cross-sectional view of the exemplary embodiment of the steam energy sensor of FIG. 17B coupled with the vessel. The figures will described in conjunction with each other.

The sensor 2 is coupled with one or more vessels 34A and 34B (generally "vessel 34") through which a flow path 36 is formed. The exemplary coupling is with a flange connection for convenience, but can be any suitable means. Fluid in the vessel 34 can be sensed by the sensor 2 using the wave launching structure 30C and the wave received structure 32C with the wave guide 24 to measure one or more energy characteristics of the fluid.

Figure 21A:
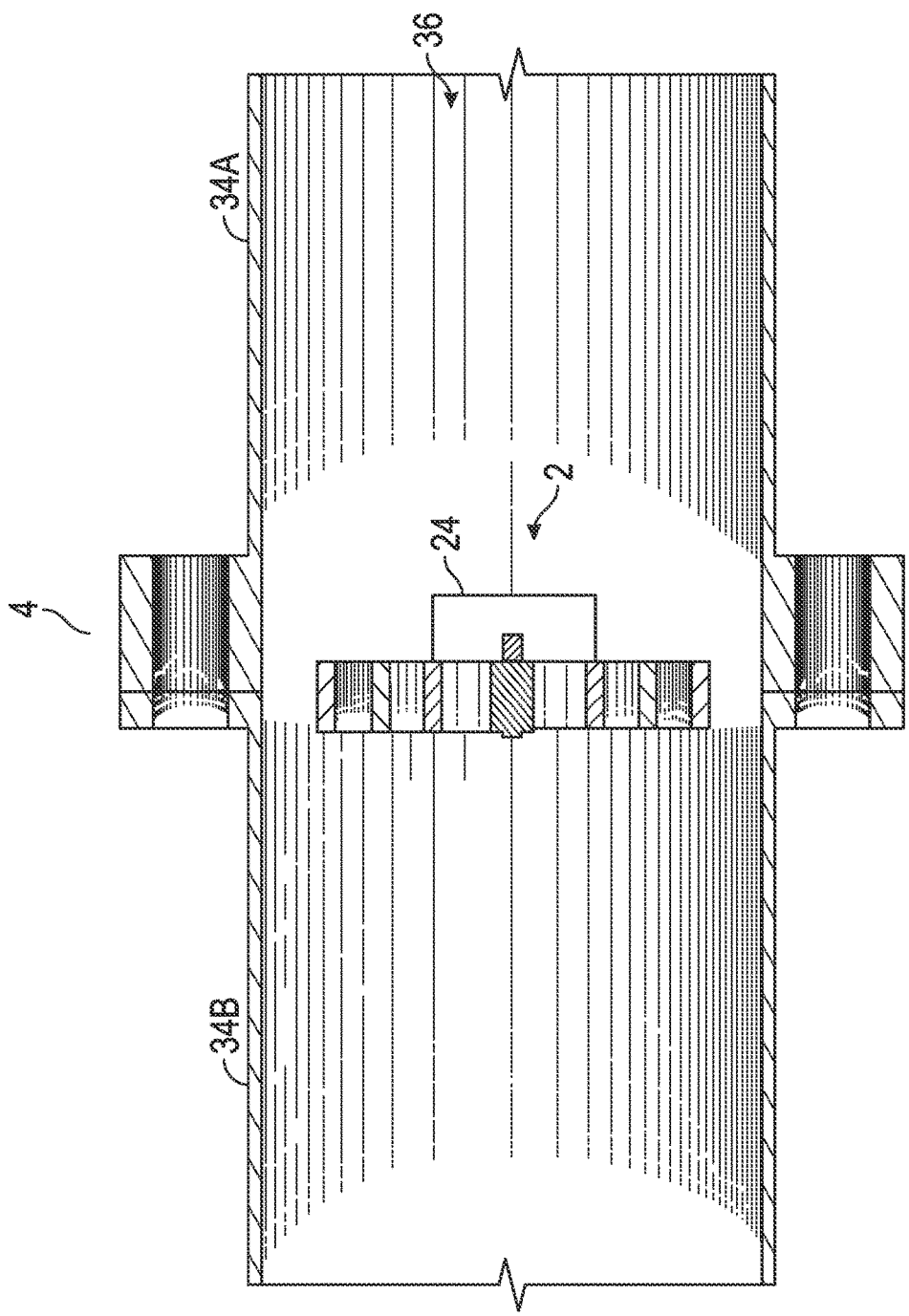
FIG. 21A is a schematic side cross-sectional view of an exemplary embodiment of the steam energy sensor coupled with a vessel.
Figure 21B:
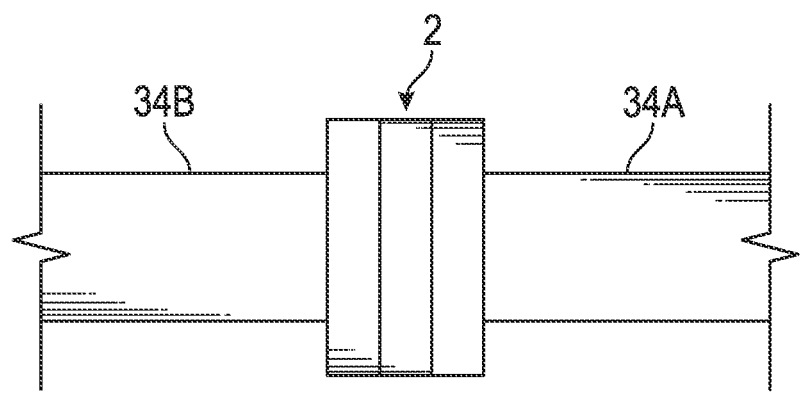
FIG. 21B is a schematic side cross-sectional view of an exemplary embodiment of the steam energy sensor coupled with a vessel.
Figure 21C:
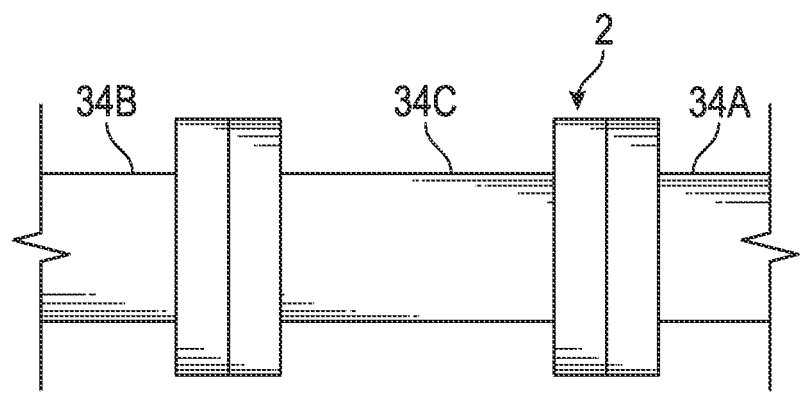
FIG. 21C is a schematic side cross-sectional view of an exemplary embodiment of the steam energy sensor coupled with a vessel.

FIG. 21A is a schematic side cross-sectional view of an exemplary embodiment of the steam energy sensor coupled with a vessel. FIG. 21B is a schematic side cross-sectional view of an exemplary embodiment of the steam energy sensor coupled with a vessel. FIG. 21C is a schematic side cross-sectional view of an exemplary embodiment of the steam energy sensor coupled with a vessel. The figures will be described in conjunction with each other. A steam energy sensor 2 can be coupled with one or more vessels 34 in a variety of ways and FIGS. 21A-21C are various nonlimiting ways. A first exemplary coupling can be formed with a portion of the vessel 34A as shown in FIG. 21A, and then the vessel 34A and 34B can be coupled in some appropriate manner with other structure, as would be known to those with ordinary skill in the art. Alternatively, the sensor 2 can be formed as an insert portion with its own vessel 34C to be placed between vessels 34A and 34B with an appropriate connection, such as a flanged connection (or threaded or welded or slip joint or other known means). As another nonlimiting example, the sensor 2 can be formed as an insert to be placed in close coupling proximity with the vessels 34A and 34B.

Further, the principles disclosed herein could be applied to other fluids. Another nonlimiting example is a chemical vapor deposition (CVD) process. CVD generally uses one or more gas precursor materials carried by an inert gas stream into a deposition vessel containing the a substrate upon which the precursor materials are to be deposited. The precursors react often by using additional energy and attach themselves to the substrate. Similar to steam energy having liquid molecules at one energy level and vapor molecules at another energy level that changes the permittivity of the vapor based on concentration, the mixture of the precursor molecules at one polarization level and the inert gas molecules at another polarization level changes permittivity of the fluid based on the concentration.

Other and further embodiments utilizing one or more aspects of the inventions described above can be devised without departing from the spirit of Applicant's invention.

Various types, sizes, and amount of components can be used to achieve a desired response. Various types of EM energy, including electric fields created by applying discrete frequencies or pulses having wide band of frequencies, can be applied to the object(s) with the material(s) to be measured. Electrical permittivity, magnetic permeability, or a combination thereof can be used to determine the characteristics to be measured. Other variations are possible.

Further, the various methods and embodiments of the sensor system and methods herein can be included in combination with each other to produce variations of the disclosed methods and embodiments. Discussion of singular elements can include plural elements and vice-versa. References to at least one item followed by a reference to the item may include one or more items. Also, various aspects of the embodiments could be used in conjunction with each other to accomplish the understood goals of the disclosure. Unless the context requires otherwise, the word "comprise" or variations such as "comprises" or "comprising," should be understood to imply the inclusion of at least the stated element or step or group of elements or steps or equivalents thereof, and not the exclusion of a greater numerical quantity or any other element or step or group of elements or steps or equivalents thereof. The device or system may be used in a number of directions and orientations. The term "coupled," "coupling, "coupler," and like terms are used broadly herein and may include any method or device for securing, binding, bonding, fastening, attaching, joining, inserting therein, forming thereon or therein, communicating, or otherwise associating, for example, mechanically, magnetically, electrically, chemically, operably, directly or indirectly with intermediate elements, one or more pieces of members together and may further include without limitation integrally forming one functional member with another in a unitary fashion. The coupling may occur in any direction, including rotationally.

The order of steps can occur in a variety of sequences unless otherwise specifically limited. The various steps described herein can be combined with other steps, interlineated with the stated steps, and/or split into multiple steps. Similarly, elements have been described functionally and can be embodied as separate components or can be combined into components having multiple functions.

The inventions have been described in the context of preferred and other embodiments and not every embodiment of the invention has been described. Obvious modifications and alterations to the described embodiments are available to those of ordinary skill in the art. The disclosed and undisclosed embodiments are not intended to limit or restrict the scope or applicability of the invention conceived of by the Applicant, but rather, in conformity with the patent laws, Applicant intends to protect fully all such modifications and improvements that come within the scope or range of equivalent of the following claims.

What is claimed is:

1. A system for determining steam energy in a vessel comprising:
    a steam energy sensor comprising one or more electromagnetic ("EM") resonators disposed at differing distances from a reference position of the sensor, the sensor being configured to be inserted into the vessel;
    a transmitter of EM energy configured to apply the transmitter EM energy to the one or more resonators in the vessel;
    a controller configured to control the transmitter EM energy;

a receiver configured to receive responsive EM energy from one or more responses from the one or more resonators in the vessel; and a processor configured to receive data on the responsive EM energy from the receiver, compare the data from the receiver with predetermined data on steam energy, and determine the steam energy of steam at the sensor.

2. The system of claim 1, wherein the vessel defines a flow path through the vessel and wherein the processor is further configured to determine a steam energy flow profile across at least a portion of the flow path with the one or more responses of the one or more resonators.

3. The system of claim 1, wherein the vessel defines a flow path through the vessel and wherein the steam energy sensor further comprises an orifice configured to cause a pressure drop through the flow path, and the system further comprising:

a first pressure sensor configured to be disposed in the flow path upstream from the steam energy sensor;

a second pressure sensor configured to be disposed in the flow path downstream from the steam energy sensor;

a processor configured to receive data on the pressures from the first and second pressure sensor and process the data to determine a mass flow rate of steam through the flow path at the sensor.

4. The system of claim 3, wherein the sensor is configured to be inserted transverse to the flow path.

5. The system of claim 3, wherein the sensor is configured to be inserted in line to the flow path.

6. The system of claim 1, wherein the resonators comprises complementary split ring resonators.

7. The system of claim 6, wherein at least two of the complementary split ring resonators have different frequencies of resonance.

8. The system of claim 1, wherein the EM energy comprises an electric field.

9. The system of claim 1, wherein the EM energy comprises a magnetic field.

10. The system of claim 1, wherein the steam energy defines at least one steam quality and wherein the processor is configured to receive data on the responsive EM energy from the receiver, compare the data from the receiver with predetermined data on steam quality, and determine the steam quality of steam at the sensor.

11. A method for determining steam energy in a vessel with a steam energy sensor comprising one or more electromagnetic ("EM") resonators disposed at differing distances from a reference position of the sensor, the sensor being configured to be inserted into the vessel; a transmitter of EM energy; a controller for the EM energy; a receiver of EM energy; and a processor, the method comprising:

controlling an application of EM energy from the transmitter;

transmitting the EM energy to the one or more EM resonators in the vessel;

receiving responsive EM energy from one or more responses of the one or more EM resonators in the vessel;

processing data on the responsive EM energy;

comparing with the processor the data of the responsive EM energy with predetermined data on steam energy; and determining with the processor the steam energy of the steam at the sensor.

12. The method of claim 11, wherein the vessel defines a flow path through the vessel and further comprising determining a steam energy flow profile across at least a portion of the flow path with the one or more responses of the one or more resonators.

13. The method of claim 11, wherein the vessel defines a flow path through the vessel and further comprising:

measuring a first pressure in the flow path upstream from the steam energy sensor;

measuring a second pressure in the flow path downstream from the steam energy sensor;

processing data on the pressures; and determine a mass flow rate of steam through the flow path at the steam energy sensor.

14. The method of claim 11, wherein the steam energy defines at least one steam quality and wherein the vessel defines a flow path through the vessel and further comprising determining a steam quality flow profile across at least a portion of the flow path with the one or more responses of the one or more resonators.

15. The method of claim 11, wherein the steam energy defines at least one steam quality and wherein comparing the data of the responsive EM energy with predetermined data on steam energy comprises comparing the data of the responsive EM energy with predetermined data on steam quality; and determining the steam energy of the steam at the sensor comprises determining the steam quality of the steam at the sensor.

* * * * *